(12) United States Patent
Graham et al.

(10) Patent No.: US 7,569,396 B1
(45) Date of Patent: Aug. 4, 2009

(54) CAFFEINE DETECTION USING INTERNALLY REFERENCED COMPETITIVE ASSAYS

(75) Inventors: Anaflor Q. Graham, Saratoga, CA (US); Carralee Hathaway, Saratoga, CA (US); Mark S. Geisberg, Arcadia, CA (US)

(73) Assignee: PurpleCow LLC, Redwood City, CA (US)

(*) Notice: Subject to any disclaimer, the term of this patent is extended or adjusted under 35 U.S.C. 154(b) by 169 days.

(21) Appl. No.: 11/530,232

(22) Filed: Sep. 8, 2006

(51) Int. Cl.
  *G01N 33/553* (2006.01)
(52) U.S. Cl. .................. 436/514; 436/20; 436/518; 436/525; 436/810; 436/816; 436/901; 435/7.1; 435/7.91; 435/7.92; 435/7.93; 435/970; 435/973; 435/975
(58) Field of Classification Search ............ 436/20, 436/514, 518, 525, 810, 816, 901; 435/7.1, 435/7.91, 7.92, 7.93, 970, 973, 975
See application file for complete search history.

(56) References Cited

U.S. PATENT DOCUMENTS

| | | | |
|---|---|---|---|
| 3,646,346 A | 2/1972 | Catt | |
| 3,857,931 A | 12/1974 | Hager | |
| 3,996,345 A | 12/1976 | Ullman et al. | |
| 4,062,733 A | 12/1977 | Edwards et al. | |
| 4,104,029 A | 8/1978 | Maier, Jr. | |
| 4,168,146 A | 9/1979 | Grubb et al. | |
| 4,181,636 A | 1/1980 | Fischer | |
| 4,264,766 A | 4/1981 | Fischer | |
| 4,313,734 A | 2/1982 | Leuvering | |
| 4,366,241 A | 12/1982 | Tom et al. | |
| 4,373,932 A | 2/1983 | Gribnau et al. | |
| 4,376,110 A | 3/1983 | David et al. | |
| 4,703,017 A | 10/1987 | Campbell et al. | |
| 4,740,468 A | 4/1988 | Weng et al. | |
| 4,775,636 A | 10/1988 | Moeremans et al. | |
| 4,837,168 A | 6/1989 | de Jaeger et al. | |
| 4,843,000 A | 6/1989 | Litman et al. | |
| 4,849,338 A | 7/1989 | Litman et al. | |
| 4,855,240 A | 8/1989 | Rosenstein et al. | |
| 4,861,711 A | 8/1989 | Friesen et al. | |
| 4,916,056 A | 4/1990 | Brown, III et al. | |
| 4,954,452 A | 9/1990 | Yost et al. | |
| 5,120,643 A | 6/1992 | Ching et al. | |
| 5,141,875 A | 8/1992 | Kelton et al. | |
| 5,212,060 A | 5/1993 | Maddox | |

(Continued)

FOREIGN PATENT DOCUMENTS

EP          0291194 A1    11/1988

(Continued)

*Primary Examiner*—Bao-Thuy L Nguyen
(74) *Attorney, Agent, or Firm*—Fenwick & West LLP

(57) ABSTRACT

Methods, compositions, and apparatus for detecting the presence of caffeine in a liquid sample are provided. In certain embodiments, an internally referenced competitive assay allows a very precise determination of a threshold value of caffeine for use in semiquantitative types of ligand-receptor assays. By using a detection means that participates in two assays, sensitivity is doubled in the maximum sensitivity range and the range can be adjusted to match the predicted concentration range of an analyte. This format and the materials described herein allow the assay to complete within three minutes. In addition, this format accommodates common attributes of liquid samples for detecting caffeine, such as the inclusion of milk or sugar in a coffee-type beverage.

6 Claims, 10 Drawing Sheets

U.S. PATENT DOCUMENTS

| | | |
|---|---|---|
| 5,229,073 A | 7/1993 | Luo et al. |
| 5,252,459 A | 10/1993 | Tarcha et al. |
| 5,451,504 A | 9/1995 | Fitzpatrick et al. |
| 5,451,507 A | 9/1995 | Skold et al. |
| 5,559,041 A | 9/1996 | Kang et al. |
| 5,591,645 A | 1/1997 | Rosenstein |
| 5,610,072 A | 3/1997 | Scherl et al. |
| 5,798,273 A | 8/1998 | Shuler et al. |
| 5,824,554 A | 10/1998 | McKay |
| 6,001,658 A | 12/1999 | Fredrickson |
| 6,103,536 A | 8/2000 | Geisberg |
| 6,153,147 A | 11/2000 | Craig |
| 6,287,875 B1 | 9/2001 | Geisberg |
| 6,368,875 B1 | 4/2002 | Geisberg |
| 6,461,873 B1 | 10/2002 | Catania et al. |
| 6,500,665 B2 | 12/2002 | Deegan |
| 6,557,484 B1 | 5/2003 | Engelman |
| 6,649,418 B1 | 11/2003 | Geisberg |
| 6,699,722 B2 | 3/2004 | Bauer et al. |
| 6,797,481 B1 | 9/2004 | Ullman et al. |

FOREIGN PATENT DOCUMENTS

| | | |
|---|---|---|
| EP | 0296724 A2 | 12/1988 |
| EP | 0323605 A2 | 7/1989 |
| WO | WO 92/12428 A1 | 7/1992 |
| WO | WO 94/01774 A1 | 1/1994 |
| WO | WO 95/01775 A1 | 1/1995 |
| WO | WO 96/27795 A1 | 9/1996 |

CAFFEINE DETECTION USING INTERNALLY REFERENCED COMPETITIVE ASSAYS

RELATED APPLICATIONS

Not applicable.

BACKGROUND OF THE INVENTION

1. Field of the Invention

The invention relates generally to methods, apparatus and compositions, useful for detecting the presence of caffeine in a liquid sample, and more specifically, for detecting the presence of caffeine in a beverage.

2. Description of the Related Art

Competitive ligand-receptor assays. Ligand-receptor assays take advantage of the ability of bioreagents to identify and quantify minute amounts of a wide range of substances, also referred to as analytes, with a high degree of specificity and sensitivity. Competitive ligand-receptor assays are one variant of ligand-receptor assays in general. In competitive ligand-receptor assays, analyte substances in the sample compete with another substance, for example a signal-producing substance, for a limited number of binding sites on the counterpart of the ligand-receptor pair. After the binding has taken place, the amount of other substance bound to the counterpart is detected by any of several means. The signal intensity of competitive ligand-receptor assay is in an inverse relationship with the concentration of analyte present; thus, a sample with no analyte will give a maximum signal intensity, and a sample with a range of analyte concentration will produce less than a maximum signal. Thus, conventional competitive ligand-receptor assays, acting alone, have a maximum sensitivity in a narrow analyte concentration range and require external calibration and standardization.

An additional disadvantage of traditional competitive ligand-receptor assays is that they require external calibration. This disadvantage manifests itself in so-called semi-quantitative assays, where a "yes" or "no" is indicated by the assay based on the presence or absence of a predetermined concentration of analyte. Such semi-quantitative competitive ligand-receptor assays are difficult to perform without external calibration, thus limiting their usefulness in a variety of important market segments. Due to the inverse relationship between signal intensity and analyte concentration, all but the most concentrated samples will give a signal in the assay, and therefore a standard curve (or at least one control point with a known standard) must be run in parallel with the sample assay to interpret accurately any reading of the sample assay. For example, an optical density reading of 0.5 in a competitive immunoassay using enzymes as a signal producing system is meaningless. However, if the user runs a known standard of, for example, 10 micrograms per milliliter of analyte and obtains a reading of 1.0, then the sample with the reading of 0.5 can be said to be more concentrated than the 10 microgram per milliliter sample. The need for standardization has severely limited the practical usefulness of current competitive ligand-receptor assays by requiring several runs of the assay to determine one sample concentration. One of the major disadvantages of the requirement for outside calibration is the concomitant reduction of precision and accuracy of each assay due to inter-assay variability in the calibration process. Furthermore, while there are commercially-available immunochromatographic test strip versions of the ligand-receptor competitive assay available that do not require external calibration, these assays are designed to give a positive indication for the analyte at the least sensitive portion of the analyte concentration versus signal intensity curve. Thus, these immunochromatographic test strips are to be interpreted as positive for analyte in the sample when no signal is seen at the test line. As one skilled in the art would recognize, the precision of the determination of analyte concentration is compromised in such an assay.

Immunoassays. One flavor of ligand-receptor assay is an immunoassay. Various known formats exist for immunoassays, including immunochromatographic test strips for detecting small molecule analytes. One format uses a competitive immunoassay, for which the result is revealed as two lines (negative result) or one line (positive result). Another format displays a single line as an indication of a positive result. Drawbacks of these formats include a very low dose-response ratio at the positive/negative cutoff concentration for some analytes, multiplicity of necessary reagents, high cost of production, and uncertain adaptability to the concentration range of interest for some analytes.

Caffeine detection assays. Immunoassays can be used to detect various analytes, including assays using anti-caffeine antibodies to detect the presence of caffeine. Existing clinical laboratory analyses and test strip formats using traditional immunoassay techniques for caffeine provide varying results. In the laboratory setting, the scientific literature includes methods such as electrometric determination in which a caffeine-specific electrode is prepared from a caffeine-picrylsulfonate ion-pair complex dissolved in octanol; fluorimetric determination in which a buffered solution of caffeine is oxidized with N-bromosuccinimide and then reacted with dimethyl o-phenylenediamine followed by a fluorescence measurement at 480 nm; colormetric determination in which an ethenolic solution of caffeine is oxidized by potassium bromate, dried and then redissolved in dimethylformamide followed by an absorbance measurement at 500 nm; Fourier Transform Infrared Spectrophotometry (FTIR); thin-layer/gas chromatography; enzyme-linked immunosorbent assays (ELISA) in which a caffeine-containing sample of plasma or serum is dissolved in a buffered solution and incubated in a vessel where it competes with peroxidase-labeled caffeine for the binding sites on caffeine antibodies followed by detection of a visible color change with the addition of o-phenylenediamine; immunoassay of theophylline with cross-sensitivity for caffeine; and immunoliposome assay of theophylline with cross-sensitivity for caffeine.

There are a number of commercially available lateral-flow type tests disclosing methods for the detection of large or small analytes, using either "typical" competitive inhibition to produce negative or indirect reporting results, i.e., reduction of signal with increasing analyte concentration, or producing positive or direct reporting results, i.e., increase in signal with increasing analyte concentration. For example, U.S. Pat. Nos. 5,229,073; 5,591,645; 4,168,146; 4,366,241; 4,855,240; 4,861,711; 5,120,643; 4,703,017; 5,451,504; 5,451,507; 5,798,273; 6,001,658; and 6,699,722. However, these types of commercially available lateral-flow type tests use either "typical" competitive inhibition to produce negative or indirect reporting results, or produce positive or direct reporting results, which share the drawbacks described above. Available tests also may take too long to produce a result to be viable.

It is relatively easy to determine the presence of a wide variety of compounds using analytical chemistry techniques. However, such methods often are not available, or practical, for individual consumers seeking to determine the presence or absence of certain compounds in their food and beverages.

For example, although "decaffeinated" coffees, teas, and soft drinks have become increasingly popular, the average consumer has no way of verifying the absence (or presence) of caffeine in such beverages when receiving them in restaurants and other public and private settings.

The rise in consumption of decaffeinated beverages has resulted in part from the health concerns of ingesting excessive amounts of caffeine. Caffeine is a bitter crystalline alkaloid. There are a variety of biological effects and symptoms caused by the ingestion of caffeine including tachycardia, diuresis, headaches, decrease in fine motor coordination, insomnia, and central neurological stimulation. Excessive amounts of caffeine can make people tense, irritable, and, in some cases, elevate the heart rate to unsafe levels. Caffeine can also irritate the alimentary canal. It is common for people diagnosed with sensitive stomachs and colons, as well as other medical conditions, to be required to refrain from ingesting caffeine as part of their medical treatment. Pregnant women may not drink any caffeinated beverages for fear of a teratogenic effect. Both men and women avoid caffeinated beverages because caffeine is a known diuretic. Also, as people age, they become increasingly sensitive to the effects of caffeine. However, an individual requesting a decaffeinated beverage can not be fully certain of the reduced level or absence of caffeine in the beverage.

The present invention addresses these and other deficiencies of the prior art as described more fully below.

SUMMARY OF THE INVENTION

The present invention is defined by the following claims, and nothing in this section should be taken as a limitation on those claims. Disclosed herein are methods, compositions, and apparatus for detecting the presence of caffeine, in a liquid sample. An internally referenced competitive assay such as described herein eliminates the above-referenced drawbacks. This dual-assay format provides for adjustment of the test for the concentration range of interest, and the internal calibration feature allows a very precise determination of a threshold value of caffeine for use in semiquantitative types of ligand-receptor assays. In addition, the dual assay eliminates the need for external calibration, while retaining the specificity and sensitivity of traditional competitive assays. By using a detection means that participates in two assays, sensitivity is doubled in the maximum sensitivity range and the range can be adjusted to match the predicted concentration range of caffeine. This format and the materials described herein allow the test to complete within three minutes. In addition, this format accommodates common attributes of liquid samples for detecting caffeine, such as the inclusion of milk or sugar in a coffee-type beverage.

BRIEF DESCRIPTION OF THE SEVERAL VIEWS OF THE DRAWINGS

These and other features, aspects, and advantages of the present invention will become better understood with regard to the following description, and accompanying drawings, where.

DETAILED DESCRIPTION OF PREFERRED EMBODIMENTS

Figure 1A:
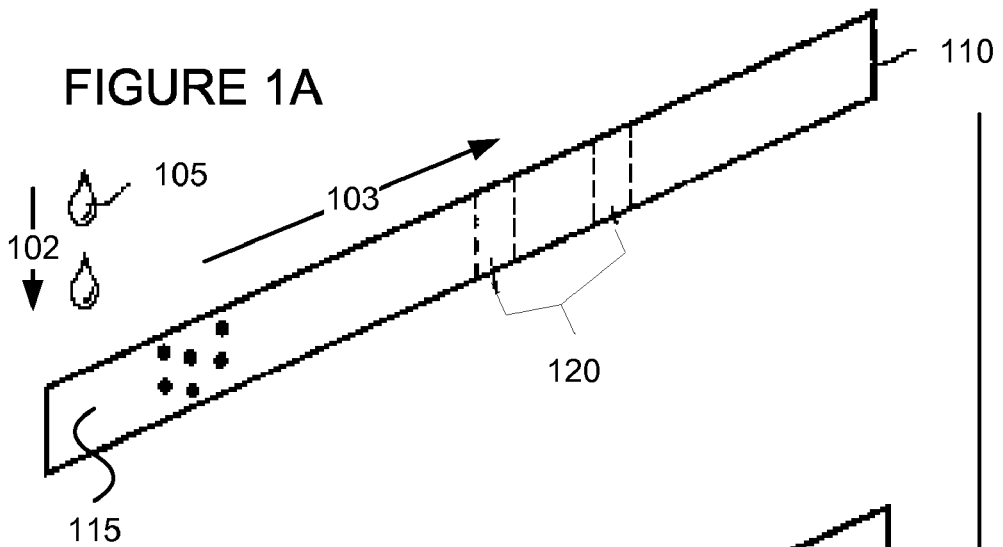
FIG. 1A ("FIG. 1A") illustrates a testing substrate with a liquid sample being applied according to one embodiment of the present invention.

Briefly, and as described in more detail below, described herein are methods, compositions and apparatus for detecting the presence of caffeine, in a liquid sample. The present invention provides a competitive assay for determining whether caffeine is present in a liquid sample. The method includes applying the liquid sample to a testing substrate and detecting a visible signal indicative of the level of caffeine present in the sample. The assay uses a ligand-receptor method that eliminates the need for external calibration to obtain an accurate result, as described in U.S. Pat. Nos. 6,649, 418, 6,368,875, 6,287,875 and 6,103,536 owned by Silver Lake Research Corporation of Monrovia, Calif., and each of which are hereby incorporated in their entirety by reference. Thus, the present invention has a detection means that participates in two assays, with the signal intensities of both assays being related to the concentration of caffeine to be determined. The signal intensity of one of the assays is inversely related to the concentration of caffeine, and the signal intensity of the second assay is directly related to the concentration of caffeine. The combined assay proceeds quickly, providing the visible signal within three minutes. In one embodiment, the ligand-receptor pair includes an anti-caffeine antibody, a caffeine analog, and caffeine if present in the liquid sample, e.g., a beverage. In this example, the assay provides at least an accurate threshold determination of whether the sample is caffeinated.

DEFINITIONS

Terms used in the claims and specification are defined as set forth below unless otherwise specified.

An "analog" of caffeine is a molecule that binds to the one member of a ligand-receptor pair in approximately the same specificity as caffeine itself.

"Bibulous" materials are materials that have the capability to effect a chromatographic separation of the contained materials, including paper, nitrocellulose, nylon and the like.

"Direct ligand-receptor pair" refers to the pair that does not contain caffeine or a caffeine analog. This pair is so named because the signal intensity generated by this pair is directly proportional to the concentration of caffeine in the sample.

The "first member" of ligand-receptor pair refers to the member bound, covalently or non-covalently, at least to a sub-population of the particles.

"Inverse ligand-receptor pair" refers to the pair of which caffeine, or a caffeine analog, is a member. This pair is so named because the signal intensity generated by this pair is inversely proportional to the concentration of caffeine in the sample.

"Ligand-receptor pair" refers to compounds having spatial and/or polar features which permit them to bind specifically to each other. Examples of ligand-receptor pairs useful in the present invention include specific binding pairs such as antigens and antibodies, or fragments of antibodies, both polyclonal and monoclonal. Members of ligand-receptor pairs may be "engineered," that is, made by synthetic means.

"Liquid Sample" means liquids or extracts suspected of containing caffeine.

"Non-bibulous" lateral flow means liquid flow in which all of the dissolved or dispersed components of the liquid are carried at substantially equal rates and with relatively unimpaired flow laterally through the membrane, as opposed to preferential retention of one or more components as would occur, for example, in materials capable of adsorbing or "imbibing" one or more components.

"Non-diffusively bound" means the second members of the inverse and direct ligand-receptor pairs are either covalently or non-covalently attached to the solid support such that advancing liquid does not cause either member of the pair to substantially move from the place it is applied on the solid support.

"Particles" can be a wide range of materials known in the art. At least one sub-population of these particles is composed of a first member of a ligand-receptor pair and a signal means, as discussed below. Thus, such particles can include enzymes such as glucose oxidase, horseradish peroxidase, alkaline phosphatase, galactosidase, or oxidoreductase. Such an enzyme, along with its signal producing system, such as described in Pawlak et al., International Patent Application No. WO 95/01775; a carbon sol, such as discussed in U.S. Pat. No. 5,559,041; erythrocyte ghosts, liposomes, and colored latex particles, such as discussed in U.S. Pat. Nos. 4,703,017 and 5,252,459; colloidal metal particles, such as colloidal gold, colloidal silver, colloidal platinum and colloidal selenium, such as discussed in U.S. Pat. Nos. 4,313,734, 4,775,636, and 4,954,452; each of these references are incorporated by reference herein in their entirety. Colorable particles and colorable latex particles are also known in the art and useful as particles herein, such as discussed in U.S. Pat. Nos. 4,373,932 and 4,837,168, both of which are incorporated herein by reference.

The "second member" of a ligand-receptor pair refers to the corresponding binding member of the pair non-diffusively bound in a signal ratio area.

"Signal means" refers to any of the conventional signaling methods known in the art detectable by methods such as visible inspection, UV and visible spectrophotometry, fluorimetry and radiation counters. In one embodiment, the signal means can be a property of the particles themselves. Alternatively, the signal means may be an inducible property of the particles, such as colorable latex particles, such a shown in U.S. Pat. Nos. 4,373,932 and 4,837,168, each incorporated by reference above. Alternatively the signal means can be attached, either covalently or non-covalently, to either the particle itself, to one or more members of the ligand-receptor pair bound to the particle, or both. Chemiluminescent molecules, such as luminol, luciferin, lucigenin, or oxalyl chloride can be used as a signal means, for example as described in U.S. Pat. No. 4,104,029, hereby incorporated by reference herein in its entirety for all purposes. Finally, enzymic systems that react with a colorless substrate to give a colored product, such as horseradish peroxidase and aminoethylcarbazole are useful as signal means.

A "testing substrate" is made of a porous material that is generally hydrophilic or capable of being rendered hydrophilic, including inorganic powders such as silica, magnesium sulfate, and alumina; natural polymeric materials such as cotton, particularly cellulosic materials and materials derived from cellulose, such as fiber containing papers, e.g., filter paper, chromatographic paper, etc.; synthetic or modified naturally occurring polymers, such a nitrocellulose, cellulose acetate, fiberglass, poly(vinyl chloride), polyacrylamide, cross-linked dextran, agarose, polyacrylate, etc.; either used by themselves or in conjunction with other materials; ceramic materials; and the like. Alternatively, the testing substrate of the present invention is fashioned from non-bibulous lateral flow material. The internally referenced assay format described herein is based on the disclosure of U.S. Pat. Nos. 6,649,418, 6,368,875, 6,287,875 and 6,103,536. Preferably, the testing substrate materials of the present invention are chosen that allow the assay to complete within three minutes of application of the liquid sample.

Methods and Apparatus of the Invention

Method

Competitive ligand-receptor assays. Ligand-receptor assays take advantage of the ability of bioreagents to identify and quantify minute amounts of caffeine, with a high degree of specificity and sensitivity. Competitive ligand-receptor assays are one variant of ligand-receptor assays in general. In competitive ligand-receptor assays, caffeine in the sample competes with another substance, for example a signal-producing substance, for a limited number of binding sites on the counterpart of the ligand-receptor pair. After the binding has taken place, the amount of other substance bound to the counterpart is detected by any of several means. The signal intensity of competitive ligand-receptor assay is in an inverse relationship with the concentration of caffeine present; thus, a sample with no caffeine will give maximum signal intensity, and a sample with a range of caffeine concentration will produce less than a maximum signal. Thus, conventional competitive ligand-receptor assays, acting alone, have a maximum sensitivity in a narrow concentration range and require external calibration and standardization. An internally referenced competitive assay such as described herein and in U.S. Pat. Nos. 6,649,418, 6,368,875, 6,287,875 and 6,103,536, eliminates the need for external calibration, while retaining the specificity and sensitivity of traditional competitive assays. By using a detection means that participates in two assays, sensitivity is doubled in the maximum sensitivity range and the range can be adjusted to match the predicted concentration range of caffeine.

Immunoassays. One variant of a ligand-receptor assay is an immunoassay. Various known formats exist for immunoassays, including immunochromatographic test strips. Included in the scope of the invention is an internally referenced competitive assay, which is based on the disclosure of U.S. Pat. Nos. 6,649,418, 6,368,875, 6,287,875 and 6,103,536. This dual-assay format provides for adjustment of the test for the concentration range of interest, and the internal calibration feature allows a very precise determination of a threshold value of caffeine for use in semiquantitative types of ligand-receptor assays.

Caffeine detection assays. Immunoassays can be used to detect caffeine using anti-caffeine antibodies to detect the presence of caffeine. A dual, internally referenced assay (based on the disclosure of U.S. Pat. Nos. 6,649,418, 6,368,875, 6,287,875 and 6,103,536) is described herein, which in the present invention allows testing to complete within three minutes. In addition, this format accommodates common attributes of liquid samples for detecting caffeine, such as the inclusion of milk or sugar in a coffee-type beverage.

Referring now to FIGS. 1A-D, they illustrate a method 102-104 for detecting the presence of caffeine in a liquid sample according to one embodiment. In one embodiment the liquid sample is a beverage served as "decaffeinated."

FIG. 1A shows a liquid sample 105 being applied 102 to a contact region 115 of a testing substrate 110. Various application methods may be used for this step. According to one embodiment, the liquid sample 105 is applied to the testing substrate 110, for example using a pipette or dropper containing the liquid sample 105. The contact region 115 is dipped into the liquid sample 105 according to another embodiment. A housing is used to apply the liquid sample 105 to the testing substrate 110 according to yet another embodiment, in which the testing substrate 110 can be at least partially contained within the housing. The architecture and materials of the testing substrate 110 are described below in conjunction with FIGS. 2A-3C and 5A-5B. Examples of housing architecture are shown in FIGS. 6A-6D.

Figure 1B:
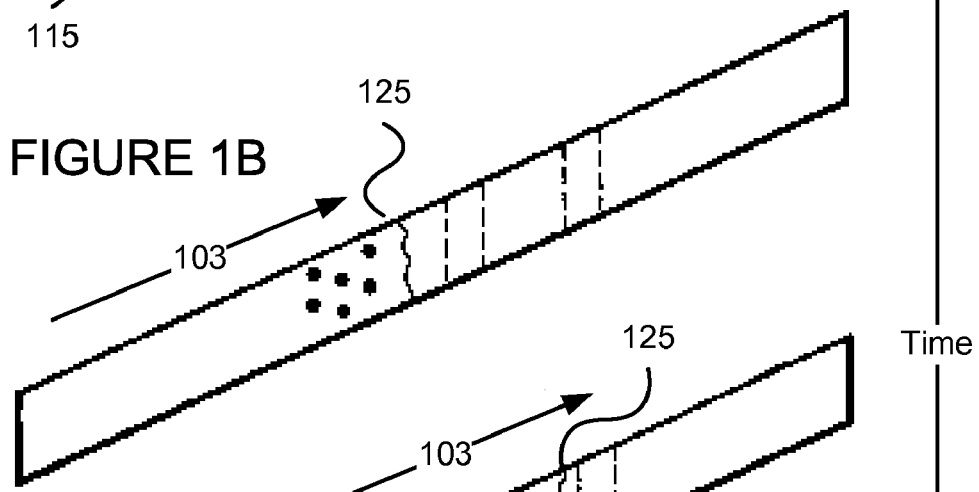
FIGS. 1B and 1C show the flow of the liquid sample across the testing substrate of FIG. 1A over time according to one embodiment of the present invention.
Figure 1C:
Figure 1D:
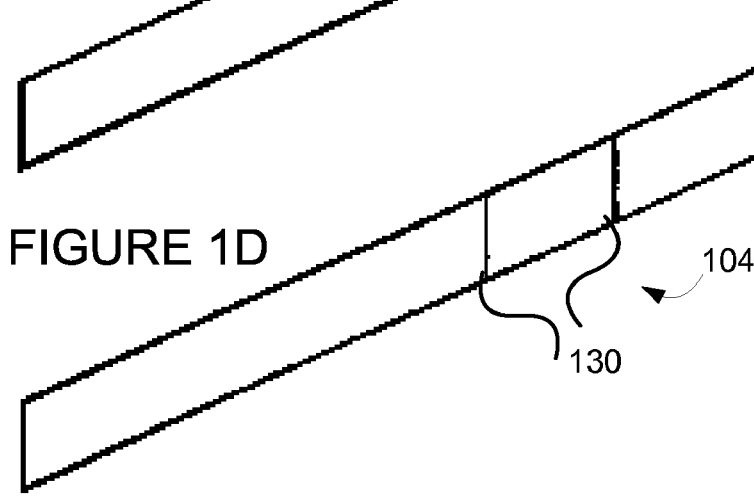
FIG. 1D illustrates a signal on the testing substrate of FIG. 1 after completion of an assay according to one embodiment of the present invention.

Referring back to FIG. 1, the liquid sample 105 flows 103 towards a signal region 120 of the testing substrate 110. The signal region 120 is spatially distinct from the contact region 115 according to one embodiment. FIGS. 1B and 1C show the flow 103 over time, as represented by a wavy line 125. A signal 130 then may be detected 104 in the signal region 120 of the testing substrate 110, as shown in FIG. 1D. Various signaling mechanisms may be used, as described below. In a preferred embodiment, the signal is visibly detectable. In other embodiments, detection of a signal and signal strength is accomplished by various methods known in the art, as described herein.

FIGS. 2A-2D and 3A-3C illustrate the mechanism for the method of FIGS. 1A-1D according to one embodiment. Many aspects of FIGS. 2A-2D and 3A-3C are not shown to scale; rather, portions are enlarged to show detail.

Figure 2A:
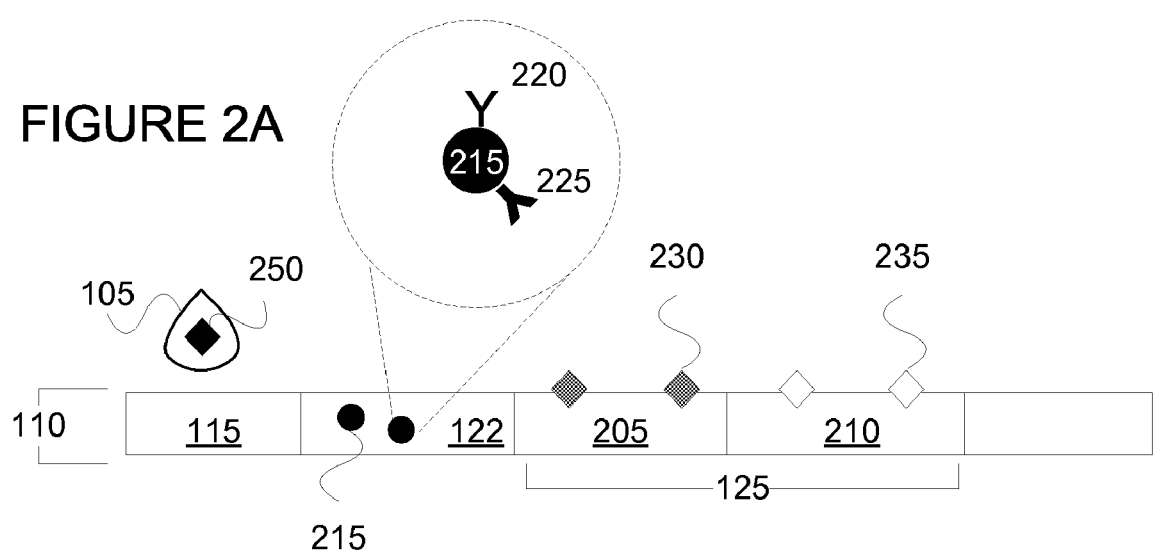
FIGS. 2A-2D and 3A-3C illustrate the method of FIGS. 1A-1D in greater detail according to one embodiment of the present invention.

FIG. 2A shows application of a liquid sample 105 to a contact region 115 of a testing substrate 110. This example corresponds to a very high level of caffeine in the sample. The testing substrate 110 also includes a particle region 122 and a signal region 125. In this example, the signal region 125 includes a first signal area 205 and a second signal area 210.

The particle region 122 further includes particles 215 diffusely bound to the testing substrate 110 as described herein. The particle 215 materials and respective qualities are further described in conjunction with FIGS. 5A-5B. A particle 215 also is shown further enlarged for clarity. The particle 215 includes a first member of an inverse ligand-receptor pair 220 ("indirect first member") and a first member of a direct ligand-receptor pair 225 ("direct first member") attached to the particle 215 surface according to one embodiment. Methods of attaching the first members 220, 225 to the particle 215 surface are discussed in greater detail below. The indirect first member 220 is an anti-caffeine antibody and the direct first member 225 is a different antibody selected such that is does not cross-react with caffeine in the example shown in FIGS. 2A-2D. In other embodiments, the indirect and direct first members 220, 225 can be any one member of an inverse ligand-receptor pair and one member of a direct ligand-receptor pair, respectively, as described herein. The particle 215 also includes a signal means as described herein.

The first signal area 205 further includes a second member of the inverse ligand-receptor pair 230 ("indirect second member") non-diffusely bound to the testing substrate 110. The second signal area 210 includes a second member of the direct ligand-receptor pair 235 ("direct second member") bound to the testing substrate 110. Methods and types of bond involved in the second member-testing substrate bond are described in greater detail in conjunction with FIGS. 5A-5B. The indirect second member 230 may be caffeine or a caffeine analog; what is important is that it acts as a competitive inhibitor of caffeine binding to indirect first member 220. The direct second member 235 is caffeine or a caffeine analog corresponding to the direct first member 225, which, in preferred embodiments is an antibody, as shown in FIGS. 2A-2D. In other embodiments, the indirect and direct second members 230, 235 can be the other member of the inverse ligand-receptor pair and the other member of the direct ligand-receptor pair, respectively, as described herein.

Figure 2B:
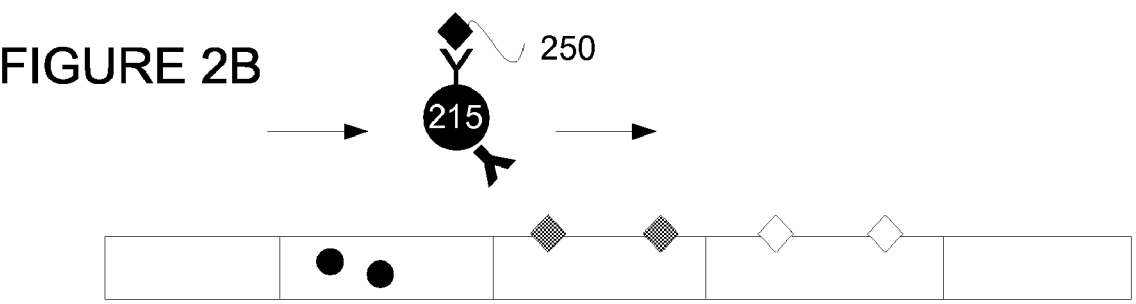
Figure 2C:
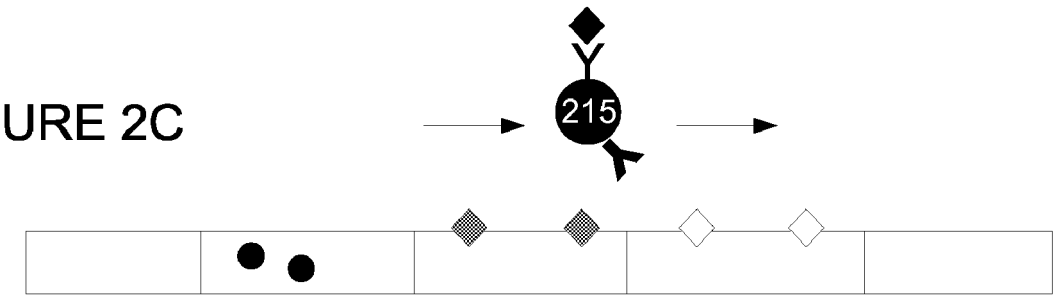
Figure 2D:
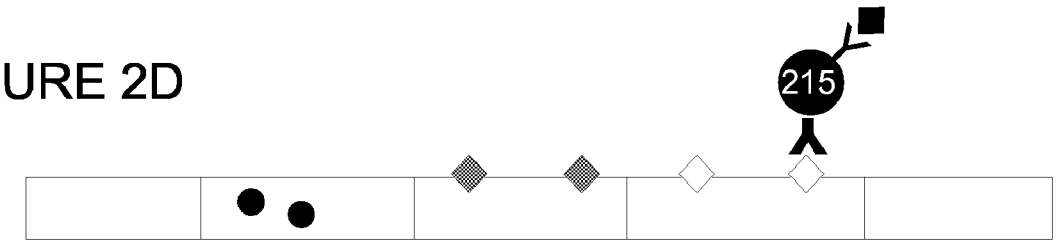
Figure 4A:
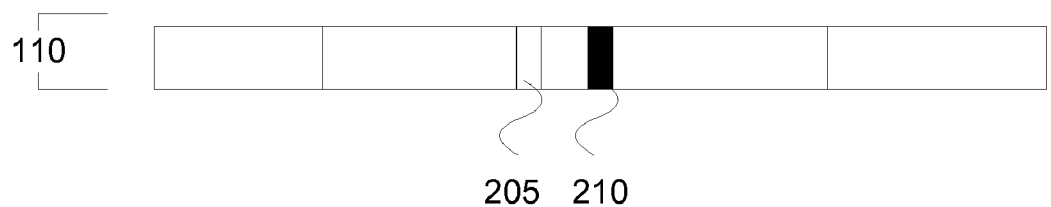
FIG. 4A illustrates a testing substrate with a signal representing a very high caffeine level according to one embodiment of the present invention.

Following application of the liquid sample 105 to the contact region 115, if the liquid sample 105 includes caffeine 250, as the sample 105 shown in FIG. 2A does, as the liquid flows across the testing substrate 110, the caffeine 250 occupies indirect first member 220 receptor sites as shown in FIG. 2B. As a result, the indirect first member 220 receptor sites are competitively inhibited from binding to the caffeine or caffeine analog 230, and the particle 215 continues past the first signal area 205 as shown in FIG. 2C. As the particle 215 reaches the second signal area 210, the direct first member 225 has open receptor sites, that are available for binding to the direct second member 235. Because the direct second member 235 is non-diffusely bound to the testing substrate 110, the particle 215 becomes immobilized when the direct second member 235 binds direct first member 225. An illustration of a testing substrate 110 with a signal corresponding to this example is shown in FIG. 4A. The first signal area 205 shows no signal, and the second signal area 210 shows a strong signal, indicative of a high caffeine level.

Figure 3A:
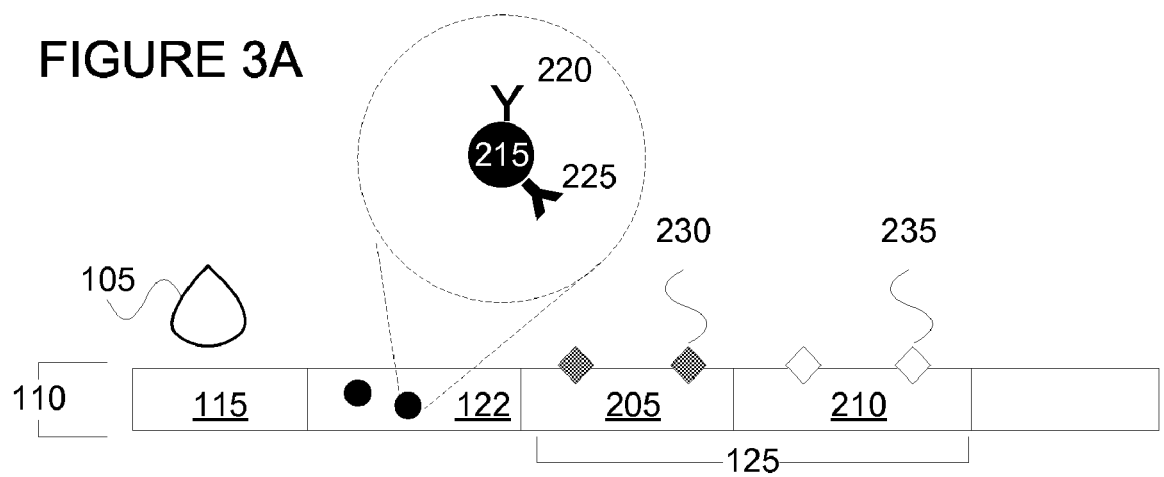
Figure 3B:
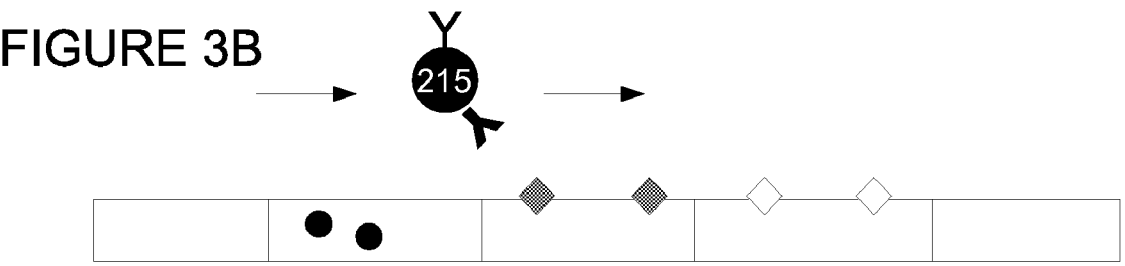
Figure 3C:
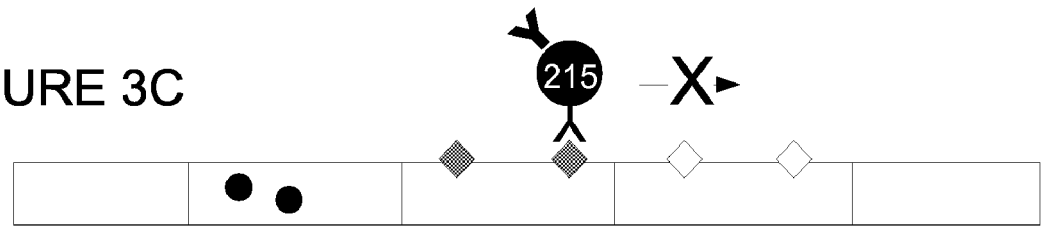
Figure 4B:
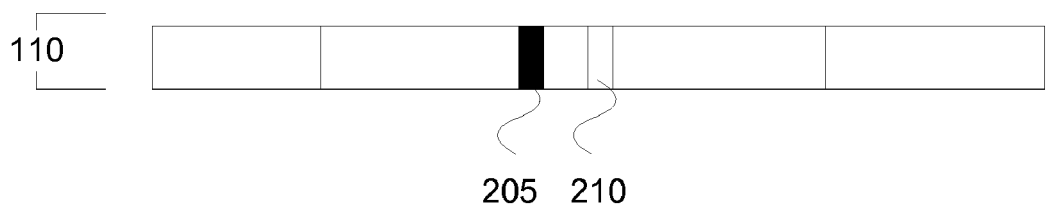
FIG. 4B illustrates a testing substrate with a signal representing a very low caffeine level according to one embodiment of the present invention.

FIG. 3A shows application of a liquid sample 105 to a contact region 115 of a testing substrate 110 similar to FIG. 2A. However, the sample 105 shown in this example has no caffeine. As the liquid flows across the testing substrate 110, no caffeine is available in the liquid sample 105 to occupy indirect first member 220 receptor sites. As a result, the indirect first member 220 receptor sites become occupied by 230 (i.e., a competitive inhibitor of caffeine for first member 220 receptor sites), and the particle 215 is immobilized in the first signal area 205 as shown in FIG. 3C As a result, the particle 215 does not continue into the second signal area 210. An illustration of a testing substrate 110 with a signal corresponding to this example is shown in FIG. 4B. The first signal area 205 shows a strong signal, and the second signal area 210 shows no signal, indicative of a very low caffeine level.

Figure 4C:
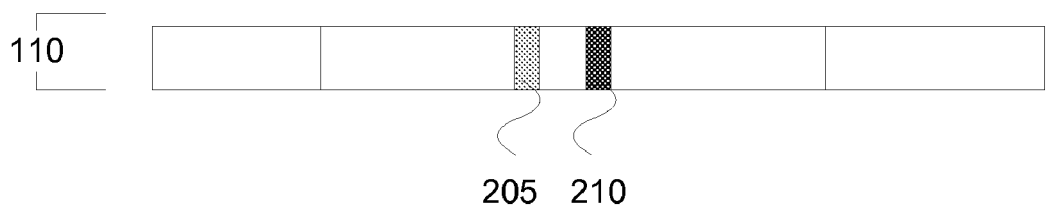
FIG. 4C illustrates a testing substrate with a signal indicating that a caffeine threshold has been exceeded according to one embodiment of the present invention.
Figure 4D:
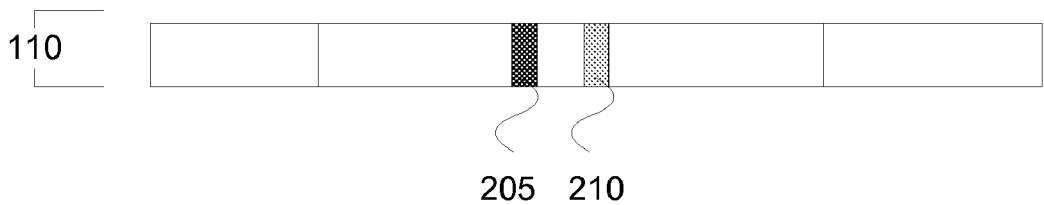
FIG. 4D illustrates a testing substrate with a signal indicating that a caffeine threshold has not been exceeded according to one embodiment of the present invention.

FIGS. 4A and 4B illustrate the two extremes of a very high amount of caffeine in a sample and a very low amount, or no, caffeine in a sample, respectively. However, there may be present in a liquid such as a beverage, a range of caffeine concentrations between concentrations that produce these two signaling extremes. FIGS. 4C and 4D illustrate two examples of other caffeine levels, in which some caffeine is present. The more caffeine present, the greater the relative number of particles 215 that bind in the second signal area 210, and the higher the signal in the second signal area 210. More caffeine also corresponds to relatively fewer particles 215 that bind in the first signal area 205, and to a lower the signal in the first signal area 205. Thus, comparing FIGS. 4C and 4D, FIG. 4C has the higher concentration level. In one embodiment, the maximum sensitivity range of the assay can be set such that the visible signal indicates whether a caffeine threshold, e.g., 15 mg/8 oz, has been met or exceeded. For example, FIG. 4C is an example of a signal indicating that the threshold has been exceeded and 4D is an example of a signal indicating that the threshold has not been exceeded. In this example, the test could be articulated that a liquid sample is caffeinated if the second signal area 210 is darker than the first signal region 205.

Figure 7:
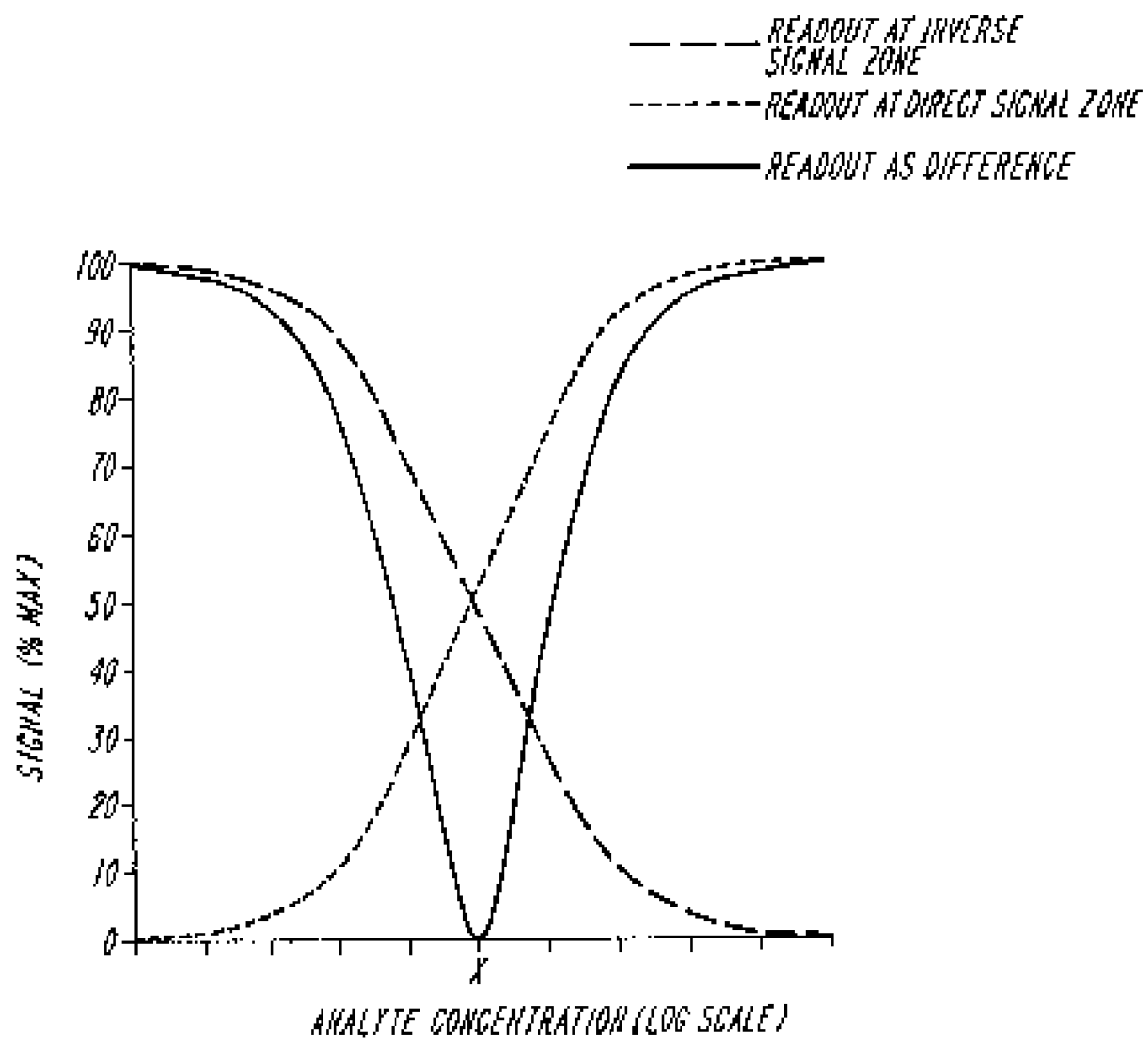
FIG. 7 illustrates the relationship between the two signals of the method of the present invention according to one embodiment.

As the signal generated in the two signal areas is related to the concentration of caffeine, the comparison will give an accurate rendering of at least a threshold, pre-determined concentration of caffeine. The relationship between the two signals is illustrated in FIG. 7. Thus, the possibilities of signal intensity ratios between the two areas set forth in Table 1 can be imagined.

TABLE 1

| Number | First Signal Area | Second Signal Area | Ratio 1st Signal/ 2nd Signal |
|---|---|---|---|
| 1 | No signal | Detectable signal | 1/∞ |
| 2 | Equal signal | Equal signal | 1 |
| 3 | Some detectable signal | No detectable signal | ∞ |
| 4 | Detectable, less than second signal area | Detectable signal, more than first signal area | <1 |
| 5 | Detectable signal, more than second signal area | Detectable, less than first signal area | >1 |

Entries 1, 3, 4, and 5 in the above Table 1 are represented in FIGS. 4A, 4B, 4C, and 4D, respectively.

Combinations of the above possible ratios can be used to determine more than one predetermined concentration of caffeine in a sample. Thus, one can control the properties of the assay components (by, e.g., selecting the relative amounts and affinities of the first and second direct and inverse ligand pair components) such that no signal in the first signal area and some in the second signal area is indicative of a first predetermined concentration threshold or range of caffeine. An equal amount of signal in both areas indicates a second predetermined concentration threshold or range and detectable signal in the first area and no detectable signal in the second area corresponds to a third predetermined concentration threshold or range. Any one or more of the above possible outcomes can be imagined to give such a multiple caffeine concentration reading.

Furthermore, the population of particles in the particle region can be manipulated to shift the range of maximum sensitivity for caffeine. Thus the population may further comprise a subpopulation of particles containing only one of the two first members of either the inverse ligand-receptor pair or the direct ligand-receptor pair, in addition to the signaling means. By this method, the signal intensity in one or the other area can be intensified independent of the concentration of caffeine.

Device Architecture

Figure 5A:
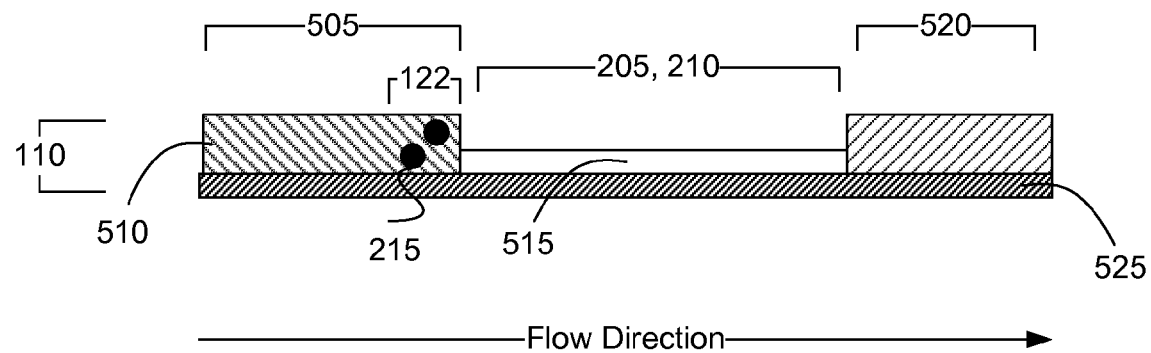
FIG. 5A illustrates a side view of a testing substrate according to one embodiment of the present invention.
Figure 5B:
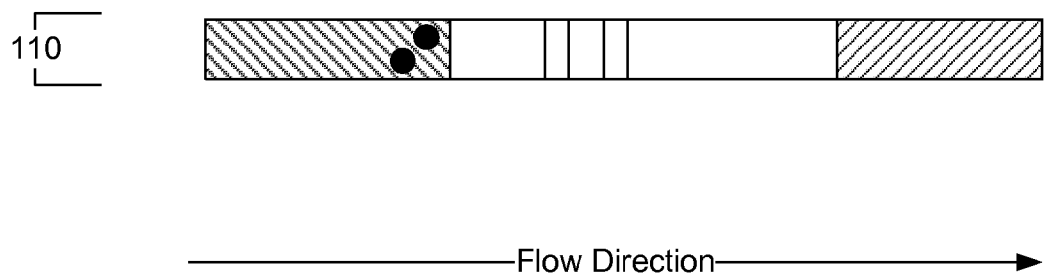
FIG. 5B illustrates a top view of a testing substrate according to one embodiment of the present invention.

An example of a device for use in conjunction with the methods described herein is represented schematically in FIGS. 5A & 5B. FIG. 5A illustrates a side view of a testing substrate 110 according to one embodiment. The testing substrate 110 includes a particle region 122 that is part of a larger sample application zone 505, as part of an optional application pad 510. These two areas are in fluid communication with the one or more signal areas 205, 210 contained on wicking material 515, which in turn are in fluid communication with an optional absorbent reservoir 520. The particle region 122, optional application pad 510, sample application zone 505, wicking material 515, the signal area(s) 205, 210 and the optional absorbent reservoir 520 comprises the testing substrate 110. In FIGS. 5A and 5B, all members of the testing substrate 110 are shown mounted in the optional backing material 525. FIG. 5B shows the particles 215 containing the first members and the signal means, are shown in the particle region 122 as they exist before application of the liquid sample. That is, they are shown as diffusively bound in an absorbent, non-particle-binding pad 510. The liquid sample is applied to the sample application zone 505 and is wicked through the signal areas 205, 210, carrying with it the particles 215. Any excess sample that is not absorbed by the rest of the testing substrate 110 along the way is eventually absorbed by the optional absorbent reservoir 525.

The two signal areas 205, 210 are placed far enough from the particle region 122 to allow sufficient binding of caffeine to the first member of the inverse ligand-receptor pair on the particle before it reaches the signal area according to one embodiment. The two signal areas are in spatial proximity as mentioned above and are close enough such that detection of each individual signal and comparison of the two signals is facilitated. It is important that the particles and the sample solution suspected of containing caffeine first go through the first signal zone before entering the second signal zone according to one embodiment. Furthermore, it is necessary that the amount of each second member bound to the solid support is greater than the total amount of the corresponding first member of a ligand-receptor pair in the population of particles for caffeine according to one embodiment. It is also important that no member of any ligand-receptor pair cross-react with any other member of a ligand-receptor pair, be it inverse or direct, or with any non-caffeine component of the liquid sample according to one embodiment. As mentioned above, the ratio of the two signal areas can be determined by visual inspection, by spectrophotometric means, or by radiation counters, or by any other method known in the art.

The testing substrate 110 referred to herein has at least two, and preferably three, zones in fluid communication with one another. Thus, as stated above, there is a sample application zone 505, which can be the same as the particle region 122, and a least one signal area 205, 210, all of which are in fluid communication with each other. It is preferred according to one embodiment that the sample application zone 505 and the particle region 122 be separate areas. These areas and the one or more signal areas 205, 210 are arranged as discussed above, and are all spatially distinct. The three areas can be arranged as a strip as shown in FIGS. 2A through 5B. The areas all can be on one piece of testing substrate, or one or more pieces support containing one or more areas, or areas can be abutted together on a suitable backing, or otherwise be made in fluid communication with each other on said backing. Thus, individual pieces of the areas can adhere to a backing by double-sided scotch tape. The backing can be, for example, plastic ribbon. See, for example, U.S. Pat. Nos. 5,591,645 and 4,861,711 and European Patent Publication No. 291 194 B1, each of which are hereby incorporated by reference herein in their entirety.

The shape of the solid support can be that of longitudinal strips, a series of parallel strips, or that of a circular configuration, wherein the circular configuration can optionally be divided into various sections. For the latter configuration, see U.S. Pat. No. 5,141,875, incorporated by reference herein. All that is required is a configuration for which the areas are arranged as discussed above, and that the sample is able to traverse them in the order discussed. Thus, for the detection of more than one analyte, a strip with a sample application zone, a particle region, and more than one signal areas, are arranged sequentially along the length of the strip, or along a radius of a non-linear configuration.

Alternatively, for each analyte, a separate series of particle regions and signal areas can be placed in parallel on one comparatively wide strip. For a circular conformation, the sample application zone would be placed at the center of the circle. In concentric rings radiating from the center, first would be the particle region and then the one or more signal areas. Alternatively, a common sample application zone could be used to supply the sample solution to two or more partitioned areas of the circular device containing separate particle regions and one or more signal areas.

The testing substrate may be porous material having pores of at least 0.1 mμ, preferably at least 1.0 mμ, which is susceptible to traversal by an aqueous medium in response to capillary force. Such materials are generally hydrophilic or are capable of being rendered hydrophilic and include inorganic powders such as silica, magnesium sulfate, and alumina; natural polymeric materials such as cotton, particularly cellulosic materials and materials derived from cellulose, such as fiber containing papers, e.g., filter paper, chromatographic paper, etc.; synthetic or modified naturally occurring polymers, such a nitrocellulose, cellulose acetate, fiberglass, poly(vinyl chloride), polyacrylamide, cross-linked dextran, agarose, polyacrylate, etc.; either used by themselves or in conjunction with other materials; ceramic materials; and the like. The testing substrate should not interfere with the signal means. This porous material can be attached to rigid or semi-rigid backing. On the other hand, the porous material may provide its own support. The porous material may be polyfunctional or be capable of being polyfunctionalized to permit covalent bonding of members of a ligand-receptor pair, as well as to permit bonding of any other components that are part of the device.

Further examples of the porous testing substrate of the present invention may be found in assays described, for example, in U.S. Pat. Nos. 4,861,711 and 5,591,645, European Patent Publication No. 291,194 and 323,605, each of which is incorporated herein by reference.

Alternatively, the testing substrate of the present invention is fashioned from non-bibulous lateral flow material. By "non-bibulous" lateral flow is meant liquid flow in which all of the dissolved or dispersed components of the liquid are carried at substantially equal rates and with relatively unimpaired flow laterally through the membrane, as opposed to preferential retention of one or more components as would occur, for example, in materials capable of adsorbing or "imbibing" one or more components. "Bibulous" materials include paper, nitrocellulose, nylon and the like, which have the capability to effect a chromatographic separation of the contained materials.

An example of the non-bibulous testing substrate material in which capillary, non-bibulous lateral flow occurs is glass fiber filter, manufactured by a number of suppliers including Whatman PLC of Middlesex, UK. This material has a typical thickness of 0.1-1 mm a density of 25-800 g/m$^2$, and a flow rate of <100 sec/5 cm. There are many other types of materials that have been used for capillary non-bibulous lateral flow, including cellulose, surface-modified cellulose, polyethylene, polyvinyl chloride, polyvinyl acetate, copolymers of vinyl acetate and vinyl chloride, polyamide, polycarbonate, polystyrene, and other polymers. Membranes formed by the classical phase inversion process may also be used. Thus, the non-bibulous solid supports, in general, will be constructed of an inert material and will optimally be less than 1 mm in thickness and allow a capillary flow rate of <100 sec/5 cm.

Bibulous materials can be converted to those which exhibit nonbibulous flow characteristics by the application of blocking agents, in particular certain detergents and proteins, which obscure the interactive forces that account for the bibulous nature of the supports per se. Thus, nonbibulous solid support materials can be comprised of bibulous materials which have been blocked. Preferred blocking agents include bovine serum albumin, either per se or in methylated or succinylated form, whole animal sera, such as horse serum or fetal calf serum, and other blood proteins. Other protein blocking agents include casein and non-fat dry milk.

Detergent-based blocking agents can also be used. The types of detergents which are appropriate are selected from nonionic, cationic, anionic and amphoteric forms, and the selection is based on the nature of the membrane being blocked. Considerations which govern the selection of the appropriate detergent blocking agent are well understood in the art. It is preferred to use detergents in combination with protein-based blocking agents. Suitable detergents which can be used either alone or in admixture with the protein blocking agents include polyoxyethylene sorbitan alcohol detergents (i.e., the Tween series), polyoxyethylene alcohols such as Nonidet P-40 or polyoxyethylene ethers such as Triton X-100. The selection of blocking agent and formulation of the blocking composition is important, as the blocking must be sufficient to effect nonbibulous flow, but the modified surface must not interfere with ligand-receptor binding.

Other embodiments of non-bibulous solid support are known in the art and can be found, for example, in Pawlak et al., International Patent Application WO 92/12428, and Sargent et al., European Patent Publication No. 296 724 B1, herein incorporated by reference.

In general, the testing substrate materials are chosen such that they enable the time to result and specificity described herein. In addition, the materials must allow the assay to proceed effectively when the liquid sample includes solution attributes that are likely to be present, such as milk, sugar, etc. Selection of these materials may proceed empirically, as parameters critical to the present invention may be found to have substantial lot-to-lot and intra-lot variability.

Alternatively, the sample application zone and the particle zone are combined and located on material different from the rest of the solid support according to one embodiment. Such optional material, hereafter referred to as an application pad, facilitates the mixing of the particles with the liquid sample before the sample migrates through the one or more signal areas. Thus, the application pad is also in fluid flow contact with the signal areas. Fluid flow contact can include physical contact of the application pad to the rest of the testing substrate, as well as the separation of the pad from the testing substrate by an intervening space or additional material which still allows fluid flow between the pad and the testing substrate. Substantially all of the application pad can overlap the testing substrate to enable the test sample to pass through substantially any part of the application pad to the proximal end of the testing substrate. Alternatively, only a portion of the application pad may be in fluid flow contact with the testing substrate. The application pad can be any material which is capable of transferring the test sample to the testing substrate and which is able to absorb a volume of sample necessary for obtaining an accurate and reproducible test result.

The testing substrate can have a sufficient inherent strength to be used without a backing material, or additional strength can be provided by means of additional backing. The testing substrate can be a single structure such as a sheet cut into strips or it can be particulate material bound to a support or solid surface such as found, for example, in thin-layer chromatography.

A backing is used for support of the testing substrate in some embodiments. The backing preferably is water insoluble, non-porous, and rigid and usually will be of the same length and width as the solid support but can be larger or smaller. A wide variety of organic and inorganic materials, both natural and synthetic, and combinations thereof, can be employed provided only that the backing does not interfere with the capillary action of the strip, or non-specifically bind assay components, or interfere with the signal means. Illustrative materials include polyethylene, polypropylene, poly(4-methylbutene), polystyrene, polymethacrylate, poly(ethylene terephthalate), nylon, poly(vinyl butyrate), glass, ceramics, metals, and the like.

The particular dimensions of the testing substrate will be a matter of convenience, depending upon the size of the sample involved, the assay protocol, the means for detecting and measuring the signal, and the like. For example, the dimensions may be chosen to regulate the rate of fluid migration as well as the amount of sample to be imbibed by porous testing substrate.

Optionally, the testing substrate can be partially or fully enclosed in a moisture-impermeable, inert casing that can be transparent, translucent, or opaque, as known in the art. Such a casing ideally has at least two apertures, one above the sample application zone and one above the signal area(s). The aperture above the signal area(s) can be covered with a transparent material. Alternatively, no apertures above the sample receiving zone are necessary if a bibulous means is provided to the exterior of the casing and to the testing substrate below the sample receiving zone such that the sample would be wicked in and applied to the testing substrate. Examples of such casings can be found in European Patent Publication No. 290 194, and as described in conjunction with FIGS. 6A-6D.

The first members of the ligand-receptor pairs may be covalently or non-covalently bound to the particles. This binding is accomplished by any method known in the art such as, for example, the use of glutaraldehyde and aminosilanes, as well as other methods described in "Immobilized Enzymes," Ichiro Chibata, Halstead Press, NY (1978); Cutrecasas, J. Bio. Chem., 245:3059 (1970); March et al., Anal. Biochem, 60:149, et seq. (1974); Cantarero et al., "The Absorption Characteristics of Proteins for Polystyrene and Their Significance in Solid phase Immunoas says," Analytical Biochemistry, 105:375-382 (1980); and Bangs, "Latex Immunoassays," J. Clin. Immunoassay, 13:127-131 (1980), Weng et al., and U.S. Pat. Nos. 4,740,468, 4,916,056, 3,857,931, 4,181,636, and 4,264,766, each of which is incorporated herein by reference. Non-covalent binding, when used, takes advantage of the natural adhesion of first members to the non-synthetic and especially the synthetic fibers. Thus, appropriately buffered solutions can be mixed with the particles then evaporated, leaving a coating of the desired first member of the ligand-receptor pair on the particle.

The particles may be applied to the particle region of the testing substrate by means known in the art. Various "printing" techniques have previously been proposed for application of such liquid reagents to carriers, for example, microsyringes, pens using metered pumps, direct printing and ink-jet printing, and any of these techniques, or other techniques that produce the same result that are yet to be discovered, can be used in the present context. To facilitate manufacture, the testing substrate can be treated with the particles and then subdivided into smaller portions (e.g., small, narrow strips each embodying the required areas and regions) to provide a plurality of substantially identical testing substrates.

In one embodiment, the signal generation can reflect a property of the particles themselves. For example, the particles may themselves intrinsically provide a detectable signal when they comprise a metal sol, a selenium sol or a carbon sol (see, e.g., U.S. Pat. Nos. 4,313,734, 4,775,636, 4,954,452, and 5,559,041 each of which is incorporated by reference herein), comprise colored latex particles (e.g., as described in U.S. Pat. No. 4,703,017, incorporated by reference above) or comprise an enzyme that has reacted with a colorless substrate to give a colored product and is encapsulated, for example, in a liposome. (See, e.g., International Patent Application No. WO 94/01774, hereby incorporated by reference herein). Alternatively, the signal may reflect an inducible property of the particles, such as colorable latex particles (e.g., as described in U.S. Pat. Nos. 4,373,932 and 4,837,168, each incorporated by reference above).

Alternatively the signal can be generated by a component that can be attached, either covalently or non-covalently, to either the particle itself, to one or more members of the ligand-receptor pair bound to the particle, or both. Such component can comprise a radioisotope, such as tritium, carbon 14, phosphorous 32, iodine 125, iodine 131, and the like. Fluorescent molecules, such as the rhodamine, fluorescein, or umbelliferone series, employed by themselves or with a quencher molecule, also can be used. (See, e.g., U.S. Pat. Nos. 3,996,345 and 4,366,241, each of which are hereby incorporated by reference herein.) Chemiluminescent molecules, such as luminol, luciferin, lucigenin, or oxalyl chloride can be used as signal generating components (see, e.g., U.S. Pat. No. 4,104,029, herein incorporated by reference). Finally, enzymic systems that react with a colorless substrate to give a colored product, such as horseradish peroxidase and aminoethylcarbazole are useful as signal generating components.

Signals detectable by visible inspection are preferred. Of these visible signals, those provided by colored microparticles are preferred.

The present first members can be covalently bound to radioisotopes such as tritium, carbon 14, phosphorous 32, iodine 125 and iodine 131 by methods well known in the art. Examples of these techniques are discussed, e.g., in H. Van Vunakis and J. J. Langone, Editors, Methods in Enzymology, Vol. 70, Part A (1980), and U.S. Pat. Nos. 3,646,346 and 4,062,733, each of which are hereby incorporated by reference herein. Similarly, the method of conjugation and use for fluorescent molecules can be found in the art. See, e.g, J. J. Langone, H. Van Vunkais et al., Methods in Enzymology, Vol. 74, Part C (1981), and U.S. Pat. Nos. 4,366,241, 3,996,345, and 4,104,029, each hereby incorporated by reference herein.

Enzymatic signaling components are known in the art and include single and dual ("channeled") enzymes such as alkaline phosphatase, horseradish peroxidase, luciferase, beta.-galactosidase, glucose oxidase, lysozyme, malate dehydrogenase, glucose-6-phosphate dehydrogenase, and the like. Examples of channeled catalytic systems include alkaline phosphatase and glucose oxidase using glucose-6-phosphate as the initial substrate. A second example of such a dual enzyme system is illustrated by the oxidation of glucose to hydrogen peroxide by glucose oxidase, which hydrogen peroxide would react with a leuco dye to produce a signal generator. For examples, see U.S. Pat. Nos. 4,366,241, 4,740, 468, 4,843,000, and 4,849,338, issued Jul. 18, 1989, each hereby incorporated herein by reference.

The substrates for the catalytic systems include simple chromogens and fluorogens such as para-nitrophenyl phosphate (PNPP), beta-D-glucose (plus optionally a suitable redox dye), homovanillic acid, o-dianisidine, bromocresol purple powder, 4-alkyl-umbelliferone, luminol, para-dimethylaminolophine, parametholxylophine, AMPPD, and the like. Preferred substrates for the enzymatic signal means are those that produce insoluble products. Examples of such preferred enzymatic signal components include aminoethylcarbazole and horseradish peroxidase; and bromochloroindolyl phosphate and nitro blue tetrazolium in conjunction with alkaline phosphate.

The procedures for coupling enzymes to the present first members are well known in the art and are described, for example, in J. H. Kennedy et al., Clin. Chim Acta, 70:1 (1976)). Reagents used for this procedure include glutaraldehyde, p-toluene diisocyanate, various carbodiimide reagents, p-benzoquinone m-periodate, $N,N_1$-o-phenylenedimaleimide, and the like.

Materials preferred for use in the optional application pad include nitrocellulose, porous polyethylene filter pads and glass fiber filter paper. The material must also be chosen for its compatibility with caffeine and assay reagents. In addition, the optional application pad can contain one or more assay reagents either diffusively or non-diffusively attached thereto. Reagents which can be contained in the application pad include buffers, preservatives, detergents, bacteriostats, ancillary ligand-receptor members, and any signal means components, such as enzyme substrates. For further discussion of such an application pad, see European Patent Publication No. 323 605 B1, hereby incorporated by reference herein.

The second members of the ligand-receptor pairs may be non-diffusively bound by direct or indirect means directly to the testing substrate. The testing substrate may have been previously derivatized prior to the application of the second member. The direct binding can be covalent or non-covalent. Covalent binding can be accomplished by using a solid support derivatized with one or more reactive groups such as amino, chloromethyl, aldehyde, carboxyl, epoxy, and the like. Covalent binding can also be accomplished by any method known in the art such as, for example, the use of glutaraldehyde, aminosilanes, cyanogen bromide, carbonyldiimidazole, ethyl chloroformate, 1-(3-nitrobenzyloxy-methyl)-pyridimium chloride (NBPC) and treslyl chloride, as well as other methods, e.g., as described in "Immobilized Enzymes," Ichiro Chibata, Halstead Press, NY (1978); Cutrecasas, J. Bio. Chem., 245:3059 (1970); March et al., Anal. Biochem., 60:149, et seq. (1974); and Tijssen et al., Practice and Theory of Enzyme Immunoassays, Chapter 3, Elsevier Science Publishers, (1985). The non-covalent binding takes advantage of the natural adhesion of second members to the non-synthetic and especially the synthetic fibers. Thus, appropriately buffered solutions can be mixed with the testing substrate then evaporated, leaving a coating of the desired second member of the ligand-receptor pair on the membrane.

The non-direct method for applying the second members to the solid support employs either covalently or non-covalently binding the second members to microparticles. Such microparticles may then be bound to or entrapped by the testing substrate such that the microparticles are within the matrix of the membrane, on the surface of the membrane, or bound to other microparticles which are in turn bound to the membrane. The size of the microparticles should be such that they do not migrate through the membrane to any significant degree. The microparticles may be made of a variety of naturally-occurring or synthetic materials, such as microparticles are those made from polyethylene, polystyrene, agarose, dextran, cellulose, starch, or the like and the aldehyde, carboxyl, amino, hydroxyl, or hydrazide derivatives thereof. The binding of the second member to the microparticle may be by methods similar to those discussed above for binding the second member directly to the testing substrate or other methods known to those skilled in the art, as discussed above for the preparation of the particles.

The second members, whether bound to a microparticle or not, can be applied to the testing substrate by the means discussed above for applying the microparticles containing the first members. In applying the second members to the solid support, it is necessary that the inverse signal area(s) span the width and the depth of the solvent front created by any fluid traversing through the testing substrate. Such fluid may be the sample solution, a wicking fluid as described below, or a solution containing the substrate for an enzymatic signal means. It is optimal, but not necessary, that the direct signal areas be the same width as the inverse signal areas.

Antibodies, and fragments thereof, suitable for use in this invention are obtained by techniques known to the art. For instance, polyclonal antibodies are obtained by immunizing a species of animal that differs from the species producing the antigen. Monoclonal antibodies are obtained by fusing the splenocytes of an immunized animal with a plasmacytoma cell line by the addition of polyethylene glycol to the cell mixture, thereby forming hybridoma cells which are suspended and then plated to tissue culture plates. Only the cultures producing antibodies that are immunologically reactive with antigen are cloned. See, e.g., U.S. Pat. No. 4,376,110, hereby incorporated herein by reference. See also Example 1 below.

In the method, the sample can be applied to the sample application zone as a viscous sample or a solid sample. Optionally, a wicking fluid can be subsequently applied to sample application zone such that caffeine is dissolved or suspended in the wicking solution and the wicking solution traverses the particle zone and the one or more signal ratio zones in the proper fashion. When an aqueous test sample is used, a wicking solution generally is not necessary but can be used to improve flow characteristics or adjust the pH of the sample solution. In general, the wicking solution used in the present invention typically has a pH range from about 5.5 to about 10.5, and more preferably from about 6.5 to about 9.5. The pH is selected to maintain a significant level of binding affinity between the members of each ligand-receptor pair. When the signal is generated using an enzyme, the pH also must be selected to maintain significant enzyme activity for color development in enzymatic signal production systems. Illustrative buffers include phosphate, carbonate, barbital, diethylamine, tris, 2-amino-2-methyl-1-propanol, and the like. The wicking solution and the sample can be combined prior to contacting the application pad or they can be contacted to the application zone sequentially.

In order to determine the ratio in the signal ratio areas, for certain of the signal generating components, it is necessary to supply separate signal generation substance, such as a substrate for an enzyme, before detecting the ratio. Thus, if the signal generating component is an enzyme that converts a colorless substrate to a colored product, (e.g., horseradish peroxidase and aminoethylcarbazole) then the substrate is applied simultaneously with or after the application of the sample solution.

As a matter of convenience, the present device can be provided in a kit in packaged combination with predetermined amounts of reagents for use in assaying for caffeine.

Where an enzyme is used as the label, the substrate for the enzyme or precursors therefor including any additional substrates, enzymes and cofactors and any reaction partner of the enzymic product required to provide the detectable signal can be included. In addition, other additives such as ancillary reagents can be included, for example, stabilizers, buffers, and the like. The relative amounts of the various reagents can be varied widely, to provide for concentrations in solution of the reagents which substantially optimize the sensitivity of the assay. The reagents can be provided as dry powders, usually lyophilized, including excipients, which on dissolution will provide for a reagent solution having the appropriate concentrations for performing the assay. The kit can also be contained in packaging material, such as air-tight foil, or various external containers known in the art. Such external containers can contain the device, reagents, and the instructions for use of the device.

Figure 6A:
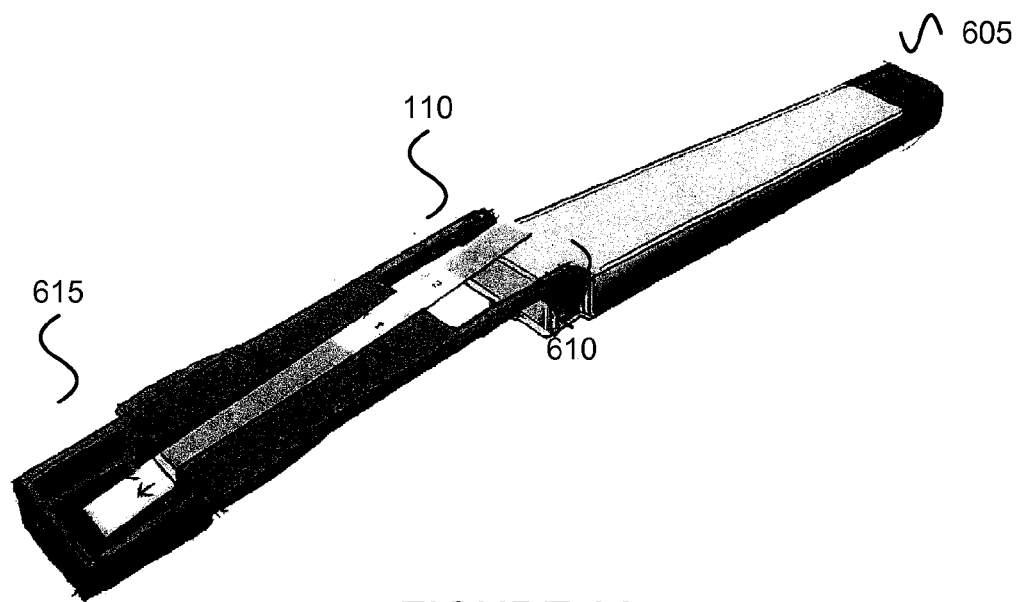
FIGS. 6A-6D illustrate examples of housings for the testing substrate according to various embodiments of the present invention.

Various embodiments of casings are within the scope of the present invention. Examples of casings, or housings, are shown in FIGS. 6A-6D. FIG. 6A is an illustration of one embodiment of a housing 605 for the testing substrate 110 of the present invention. In this example, the housing 605 foldable, e.g., about a hinge 610, for more compact storage. The folded housing 605 is stored further enclosed within a case according to one embodiment, along with testing substrates 110. The housing 605 of this example includes a receptacle 615 for obtaining the liquid sample for the assay. The testing substrate 110 is placed upon the housing 605 once the sample is obtained according to one embodiment, preferably on a flat surface. In the embodiment depicted in FIG. 6A, the receptacle 615 is designed to allow an appropriate amount of the liquid sample to be applied to the testing substrate 110.

Figure 6B:
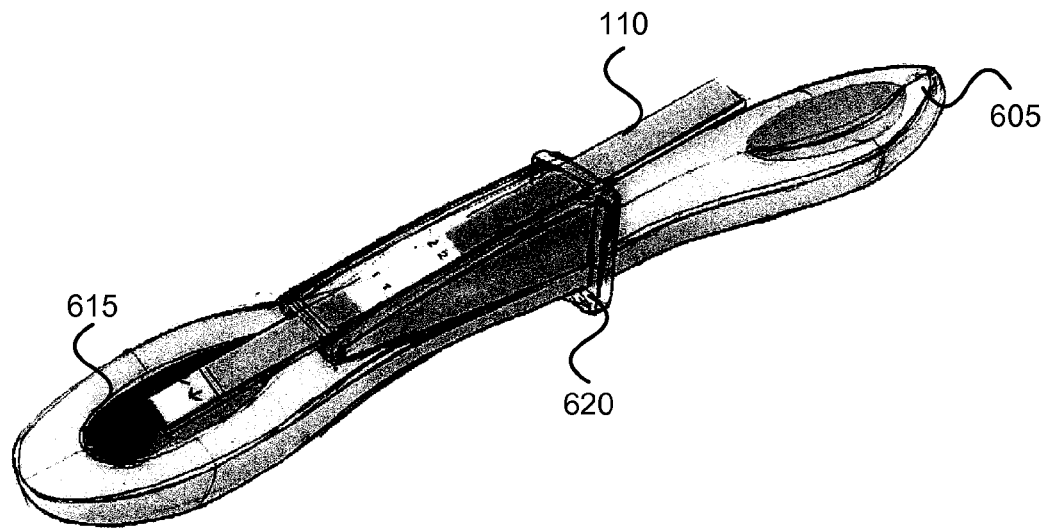

FIG. 6B shows another embodiment of a housing 605, in which the housing is shaped to resemble a spoon. The housing 605 shown in FIG. 6B also includes a receptacle 615 for use as described above according to one embodiment, and may also have a case. The housing 605 of FIG. 6B includes a transparent compartment 620 for insertion of the testing substrate 110, and to hold the testing substrate 110 in place during the assay according to one embodiment.

Figure 6C:
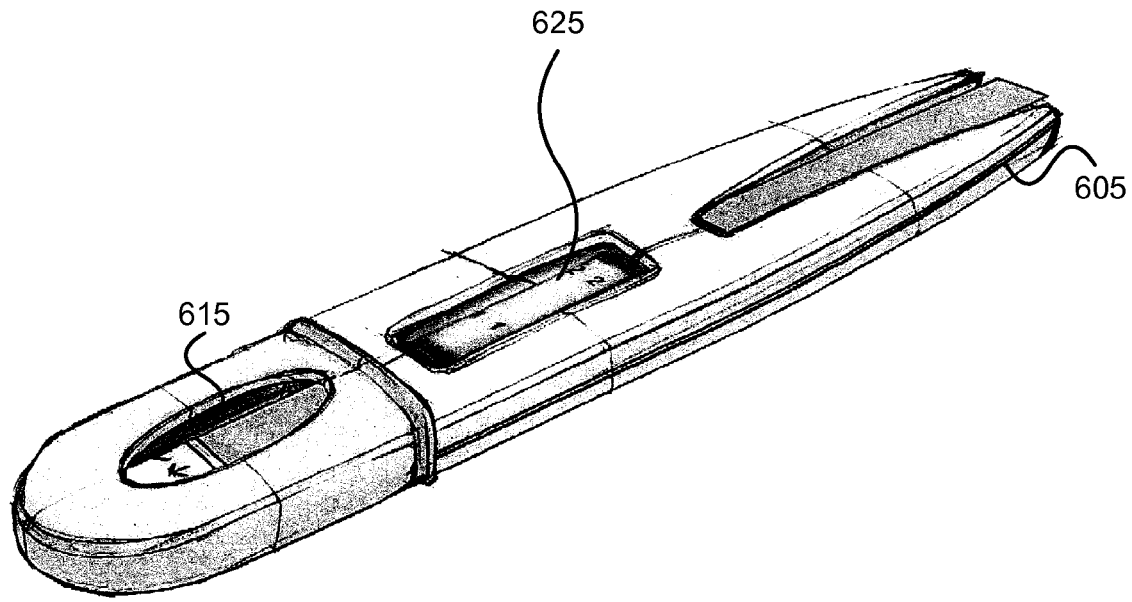

FIG. 6C shows yet another embodiment of a housing 605. In this example, the receptacle 615 of the housing 605 is dipped into the liquid sample for collection of an appropriate amount for the assay. If the housing 605 is opaque, as shown in FIG. 6C, a viewing window 625 in included so that results of the assay may be easily seen according to one embodiment.

Figure 6D:
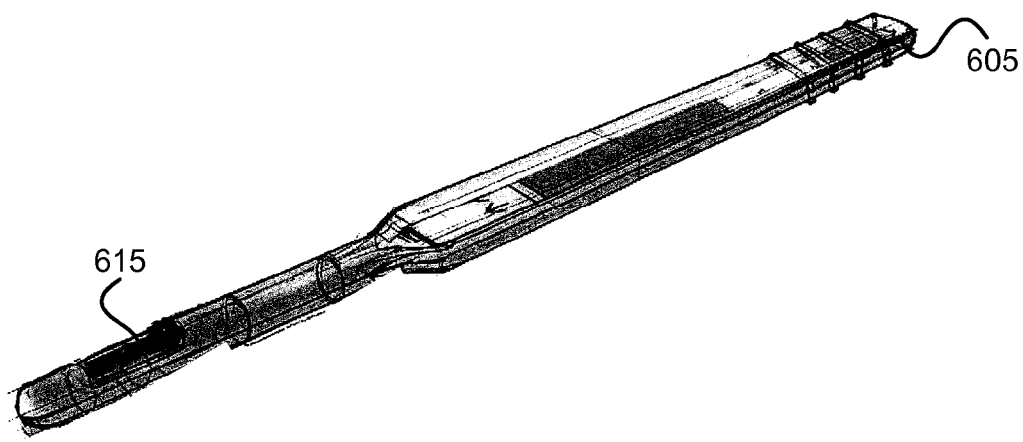

FIG. 6D shows yet another embodiment of a housing 605. Like the example in FIG. 6D, this example has a receptacle 615 that is dipped into the liquid sample for sample collection. If the housing 605 is transparent, as shown in FIG. 6D, no viewing window is required according to one embodiment.

The invention can be better understood by way of the following examples which are representative of the preferred embodiments thereof, but which are not to be construed as limiting the scope of the invention.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current edition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, $18^{th}$ Edition (Easton, Pa.: Mack Publishing Company, 1990); Carey and Sundberg *Advanced Organic Chemistry* $3^{rd}$ Ed. (Plenum Press) Vols A and B (1992).

Example 1

Development of Anti-Caffeine Antibodies

Anti-caffeine monoclonal antibodies (MAb) were produced with regard to acceptance criteria that included high-affinity binding to caffeine, minimal cross-reactivity with non-caffeine alkaloids found in coffee (e.g., theophylline, theobromine, etc.), isotypes that allow for cost-effective production of purified monoclonal antibodies, and production of hybridoma cell lines that secrete high levels of MAb.

To synthesize caffeine immunogens and immunize mice, sera from immunized mice were screened for caffeine-binding antibodies by a competitive ELISA modeled on previously described protocols, e.g., as described in Fickling, S. A. et al., "Development of an Enzyme-linked Immunosorbent Assay for Caffeine," *J. Immunol. Meths.*, 129(2): 159-64 (1990). Briefly, BSA-caffeine conjugates were synthesized using standard methods, including the linkers DSS, EMCS-IT, and others. These methods are described, e.g., in Wong S S, Wong L J., "Chemical Crosslinking and the Stabilization of Proteins and Enzymes," *Enzyme Microb. Technol.*, 14(11): 866-74 (1992); Mattson, G., et al., "A Practical Approach to Crosslinking," *Molecular Biology Reports*, 17, 167-183 (1993); and Partis, M. D., et al. (1983), "Crosslinking of Proteins by omega-maleimido alkanoyl N-hydroxysuccinimide Esters," *J. Protein. Chem.*, 2, 263-277 (1983). The BSA-caffeine conjugates were used in ELISA according to standard ELISA protocols, e.g., as described in Harlow & Lane. Antibodies: A Laboratory Manual. Cold Spring Harbor Laboratory, Cold Spring Harbor, N.Y., 1988. BSA-caffeine conjugate was coated onto high protein-binding EIA plates, incubated with serum samples with and without the presence of free caffeine, and antibody binding was detected using alkaline-phosphatase-linked goat anti-mouse-immunoglobulin (Ig) antiserum, followed by incubation with p-nitrophenyl phosphate. Substrate conversion rate was measured by optical density at 405 nm. Anti-caffeine antibodies were identified by decreased binding to BSA-caffeine when free caffeine was present.

Hybridomas producing MAbs fitting these acceptance criteria were selected, expanded, and preserved in cryobanks. MAbs for use in development of the caffeine test strips were purified from secretions of these hybridomas. After identification of mice with high titers of anti-caffeine antibodies, fusions were performed to isolate hybridomas secreting anti-caffeine antibodies. Such hybridomas were identified by screening hybridoma cell culture supernatants using the same competitive immunoassay.

Four hybridomas secreting anti-caffeine antibodies were identified, subcloned to generate stable cell lines, and cryopreserved. These hybridomas/antibodies are referenced herein as 672-1, 672-2, 672-3, and 672-4. Results from competitive immunoassays of these antibodies are shown in Table 2.

TABLE 2

| MAb | OD, No Caffeine | OD, With Caffeine |
|---|---|---|
| 672-1 | 1.004 | 0.077 |
| 672-2 | 0.876 | 0.055 |
| 672-3 | 0.664 | 0.021 |
| 672-4 | 1.114 | 0.223 |

Table 2 shows binding of antibody-containing hybridoma supernatants to BSA-caffeine with and without the presence of free caffeine (100 ug/ml). Data is shown as mean optical density (OD) at 405 nm after subtraction of buffer-only blank.

The isotype of these antibodies was determined using a commercial kit available from SouthernBiotech of Birmingham, Ala. All of the antibodies were shown to have the IgG isotype, well suited for facile purification. Furthermore, binding of antibodies to various components of the immunochromatographic test strip has been optimized, e.g., as reviewed in Bangs, L. B., *Pure & Appl. Chem.*, 68(10):1873-79 (1996).

Figure 8:
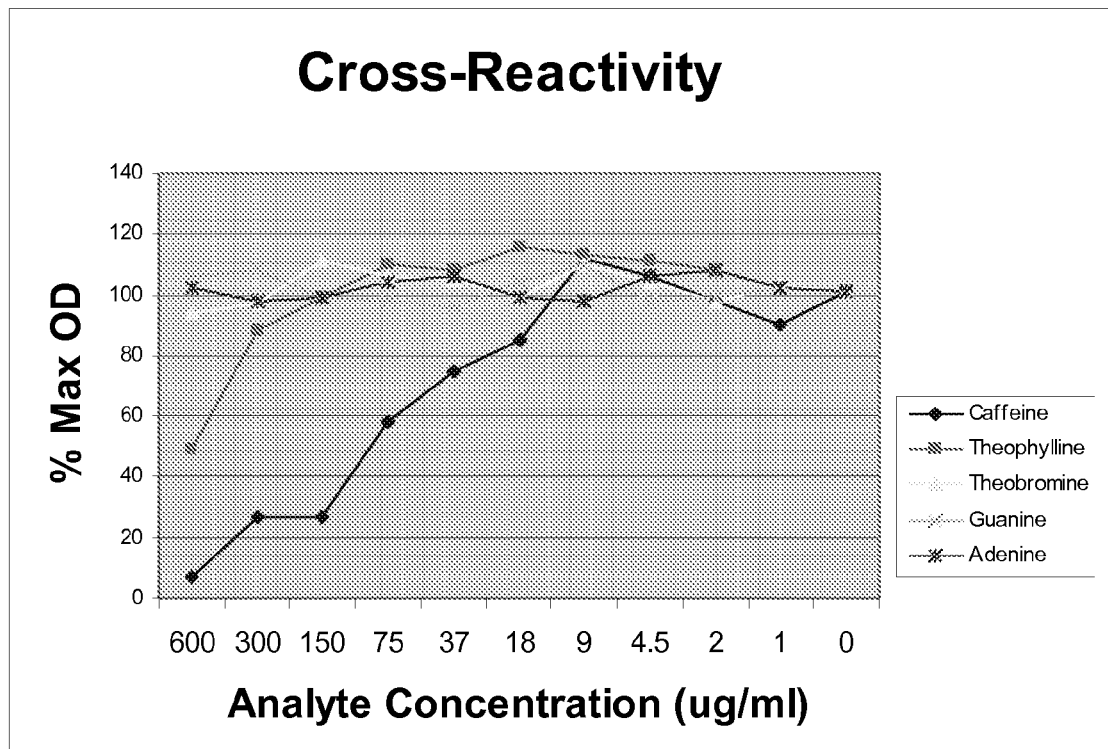
FIG. 8 is a graph showing the cross-reactivity of an antibody according to one embodiment of the present invention.

If an antibody has a very high level of cross-reactivity with any of these alkaloids, it may be undesirable for a caffeine test kit: when a sample contains very low levels of caffeine but high levels of the cross-reactant, this would lead to a false indication of caffeine concentration. The cross-reactivity of each antibody with other alkaloids normally contained in coffee was determined, including theophylline, theobromine, guanine, and adenine. The level of cross-reactivity was determined with the same competitive ELISA, using each alkaloid as the competitor in place of caffeine. Data from a representative experiment is shown in FIG. 8 (testing of antibody 672-1). None of the antibodies showed any significant cross-reactivity with any of the tested alkaloids.

Anti-caffeine MAbs 672-1 through 672-4 were further tested for use within the methods described herein. The sensitivity of each antibody for caffeine in the competitive immunoassay was analyzed. This was accomplished by varying the concentration of free caffeine while the concentration of antibody remained constant. In determinations of receptor binding affinity of a ligand using a competitive binding curve, the IC50 is the concentration required for 50% inhibition; antibodies can be compared to each other by the IC50 of each antibody's dose-response curve in a competitive assay. See descriptions of statistical analysis of immunoassay data in: Kurtz, D. A., et al., eds., "New Frontiers in Agricultural Immunoassay," AOAC International, Arlington, Va. (1995). Results of these assays are shown in Tables 3A and 3B, and FIGS. 9A and 9B, respectively.

TABLE 3B

| MAb | Conc. 0 | 1 | 10 | 100 | 1000 | 10000 | IC50 (ug/ml) |
|---|---|---|---|---|---|---|---|
| 672-2 | 100 | 99 | 83.9 | 44.7 | 21.2 | 5.6 | 78 |
| 672-3 | 100 | 102 | 71.1 | 67 | 55.5 | 21.7 | 1200 |

Tables 3A and 3B. IC50 determination of anti-caffeine MAbs. Data shown as percent maximal binding (binding at 0 ug/ml caffeine).

Figure 9A:
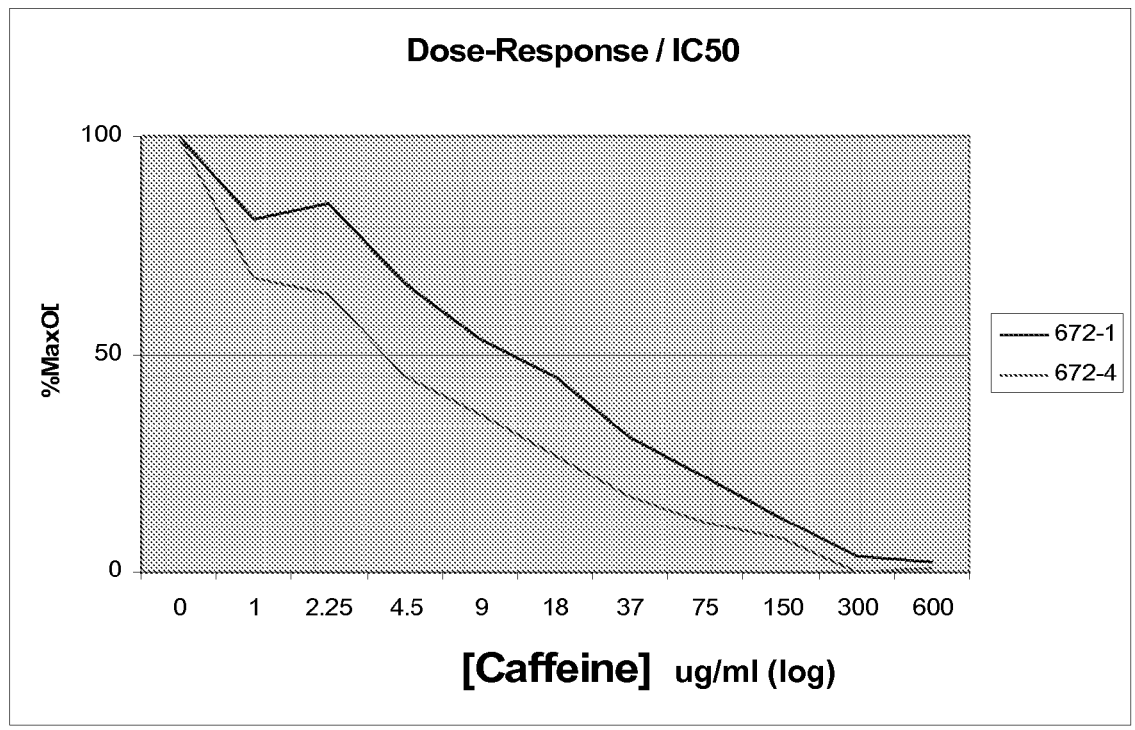
FIGS. 9A and 9B illustrate the IC50 of dose-response curves for four antibodies according to one embodiment of the present invention.
Figure 9B:
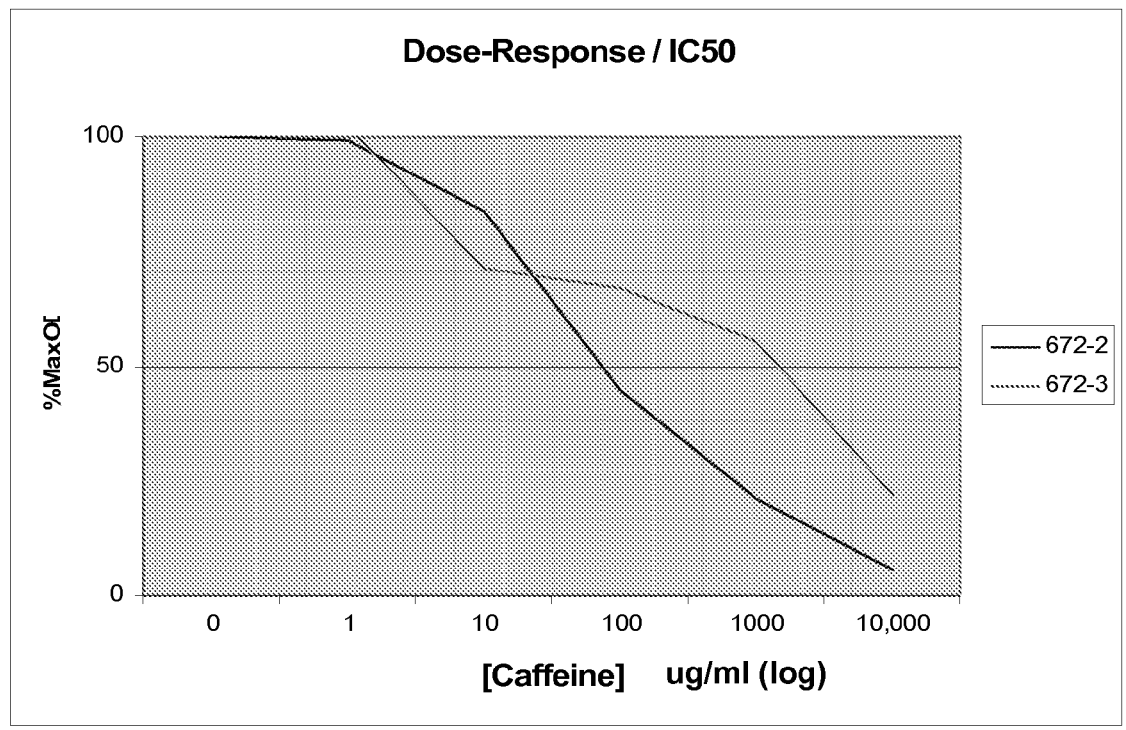

As shown in FIGS. 9A and 9B, each of the four MAbs shows a distinct IC50, bracketing the stated caffeinated/decaffeinated distinction criterion of 62.5 ug/ml (15 mg/8 oz). Antibody 672-3 had an estimated IC50 (78 ug/ml), closest to the distinction criterion. The antibody designated as 672-3 is commercially available from Silver Lake Research Corporation of Monrovia, Calif.

Example 2

Selection of Testing Substrate Materials

Immunochromatographic test strips were originally developed and marketed for home pregnancy testing in the 1980's. The industry has evolved to incorporate a variety of applications, and many suppliers have developed materials, manufacturing modules, and other solutions for a generalized immunochromatographic test strip, enabling companies to develop new products quickly and efficiently. Off-the shelf components were combined and adapted through industry-standard empirical testing for use in the methods described herein.

The generalized form of a lateral flow immunochromatographic test strip is shown in FIGS. 5A and 5B. Reviews on the theory and practice of immunochromatographic test strips, the function of each component, the positioning of reagents, and other aspects have been published. See, e.g., Bangs L. B. and Meza, M., *IVD Technology* (1994-1995); "Rapid Lateral Flow Tests," Millipore Corporation, Bedford, Mass. (2002); "The Latex Course," Bangs Laboratories, Inc., Fishers, Ind. (1994).

The starting point for development of the caffeine immunochromatographic test strip was the Watersafe® Pesticide Test, manufactured by Silver Lake Research Corp., of Monrovia, Calif., which is a lateral flow immunochromatographic test strip developed to detect a small molecule analyte in liquid samples. It was found that the components used for the Watersafe® Pesticide Test did not perform optimally when the sample was any of several types of coffee beverages, including latte and cappuccino. These coffee matrices were slow to wick, sometimes clogged the membranes completely, and produced inconsistent results at any given time point.

TABLE 3A

| MAb | Conc. 0 | 1 | 2.25 | 4.5 | 9 | 18 | 37 | 75 | 150 | 300 | 600 | IC50 (ug/ml) |
|---|---|---|---|---|---|---|---|---|---|---|---|---|
| 672-1 | 100 | 81 | 84.4 | 65.9 | 53.3 | 44.9 | 30.8 | 21.9 | 12.2 | 3.5 | 2.2 | 12 |
| 672-4 | 100 | 67.2 | 63.7 | 44.9 | 36.3 | 26.8 | 17.1 | 11.1 | 7.6 | 0.2 | 1 | 4 |

Materials available from manufacturers of flow media for immunochromatographic test strips were tested to determine a viable alternative.

Suppliers of materials for immunochromatographic test strip components provide some basic information with regard to each version of each type of material. Literally hundreds of versions of each component are available from various manufacturers worldwide. Table 4 shows the types of materials available for each component and the quantifiable properties of each provided by manufacturers.

TABLE 4

| Component | Example of material | Properties | Examples of Manufacturer |
|---|---|---|---|
| Backing | Vinyl, polyester | Thickness, adhesive type, rigidity, printability | Millipore Corp., Billerica, MA; G&L Precision Die Cutting, Inc., San Jose, CA |
| Binding Membrane | PVDF, Nitrocellulose | Porosity, thickness, flow rate, protein binding capacity | Whatman PLC, Middlesex, UK; Sartorius AG, Goettingen, Germany; Millipore Corp., Billerica, MA |
| Sample Media | Paper, Glass Fiber, Foam | Density, thickness, water absorbency, flow rate, air permeability | Whatman PLC, Middlesex, UK; Ahlstrom Paper Gorup, Mt. Holly Springs, VA; Millipore Corp., Billerica, MA |
| Reservoir Pad | Paper, foam | Density, thickness, water absorbency | Whatman PLC, Middlesex, UK; Ahlstrom Paper Gorup, Mt. Holly Springs, VA; Millipore Corp., Billerica, MA |
| Protective Cover | Acrylic | Clarity, rigidity, adhesive type | Various printing companies |

Table 4. Material choices for immunochromatographic test strip components.

Notably, there is substantial lot-to-lot and intra-lot variation in parameters, such as flow rate, from all manufacturers. Selection of these materials therefore proceeded empirically, by trying several batches of each type of component from several manufacturers. Multiple batches of binding membrane, sample media, and reservoir pads from several manufacturers were tested for compatibility with the methods described herein. For the tested components, even when reported porosity, flow rate, and other parameters were identical or in the same range, different results were sometimes seen for the coffee samples. Components were tested by substitution of each version from each manufacturer in the appropriate position within the test strip architecture, and by determination of the overall effect of each substitution by running the assay on a variety of coffee matrices.

According to one embodiment, the test strip was comprised of an adhesive-coated vinyl backing with a thickness of 0.3 mm, a nitrocellulose binding membrane with a flow rate of 90 sec./4 cm, a sample media made of a glass fiber filter 0.6 cm thick with a density of 260 g/m$^2$, a reservoir pad of cellulose wick, thickness of 1 mm, and a water absorption capacity of 1000 g/m$^2$, and a protective cover of a printable acrylic cover material with a thickness of 5 mm.

Example 3

Testing of Coffee Samples

"Decaffeinated" coffee samples were ordered between the hours of 3 p.m. and 9 p.m. over the course of approximately forty days. Samples were collected from 100 restaurants and specialty coffee retailers. The caffeine concentration in these samples was tested by high performance liquid chromatography (HPLC); assays using the testing substrate from above were run simultaneously on the same samples. The data from these tests are shown in Appendix A. Table 5 shows a statistical analyses of the results, showing the value of the caffeine assay in detecting non-decaffeinated coffee served as decaffeinated.

TABLE 5

| HPLC Data | | MAb Assay | |
|---|---|---|---|
| Mean | 23.70 | Count | 100.00 |
| Minimum | 1.55 | Correct vs. HPLC | 96.00 |
| Maximum | 325.10 | Percent correct | 96% |
| Count | 100.00 | Percent correct (true caff) | 96.00 |
| True Caffeinated | 25 | Percent correct (true decaf) | 96.00 |
| True Caffeinated (%) | 25% | | |
| True Decaffeinated | 75 | | |
| True Decaf (%) | 75% | | |

Table 5 shows that about 25% of coffee samples served as "decaffeinated" contained caffeine above the U.S. standard for decaffeinated beverages. The data shows that the MAb assay described herein accurately identified both decaffeinated and caffeinated coffees 96% of the time.

Example 4

Testing of Tea Samples

Samples of caffeinated and decaffeinated tea are tested per the parameters outlines above for coffee testing. Lipton brand Black Tea is used for the caffeinated tea samples and Twinings brand Pure Camomile tea is used for the decaffeinated tea samples. For each test, single tea bags each are placed in 6 oz. Styrofoam cups, and 8 oz. of boiling (100° Celsius) water is added to each cup. The teas each are allowed to brew for 5 min. The testing shows that the MAb assay described herein accurately distinguishes decaffeinated and caffeinated teas.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

Hybridoma 672-3, secreting native monoclonal antibody 672-3, was deposited on Oct. 10, 2008, with the American Type Culture Collection (ATCC), 10801 University Blvd., Manassass, Va. 20110-2209, under the provisions of the Budapest Treaty on the International Recognition of the Deposit of Microorganisms for the Purpose of Patent Procedures, and assigned accession number PTA-9544.

APPENDIX A

Coffee Shops

| Restaurant | Location | HPLC Result (mg/8 oz) | SLRC Test Strip Result (Caf/Decaf) |
|---|---|---|---|
| Noah's Bagels | Pasadena | 25.7 | CAF |
| Wild Oats Market | Pasadena | 10.0 | DECAF |
| Bristol Farms | Pasadena | 4.0 | DECAF |
| Border's Bookstore | Pasadena | 5.7 | DECAF |
| Coffee Bean 1 | various | 1.5 | DECAF |
| Coffee Bean 2 | various | 6.1 | DECAF |
| Coffee Bean 3 | various | 8.8 | DECAF |
| Coffee Bean 4 | various | 4.8 | DECAF |
| Coffee Bean 5 | various | 7.2 | DECAF |
| Coffee Bean 6 | various | 5.6 | DECAF |
| Coffee Bean 7 | various | 140.7 | CAF |
| Starbucks Coffee 1 | various | 7.3 | CAF |
| Starbucks Coffee 2 | various | 5.7 | DECAF |
| Starbucks Coffee 3 | various | 3.1 | DECAF |
| Starbucks Coffee 4 | various | 6.8 | CAF |
| Starbucks Coffee 5 | various | 5.3 | DECAF |
| Starbucks Coffee 6 | various | 8.3 | DECAF |
| Starbucks Coffee 7 | various | 7.6 | DECAF |
| Starbucks Coffee 8 | various | 3.4 | DECAF |
| Starbucks Coffee 9 | various | 2.9 | DECAF |
| Starbucks Coffee 10 | various | 2.9 | DECAF |
| Starbucks Coffee 11 | various | 4.7 | DECAF |
| Starbucks Coffee 12 | various | 3.2 | DECAF |
| Starbucks Coffee 13 | various | 3.6 | DECAF |
| Starbucks Coffee 14 | various | 2.1 | DECAF |
| Starbucks Coffee 15 | various | 3.8 | DECAF |
| Starbucks Coffee 16 | various | 3.1 | DECAF |
| Starbucks Coffee 17 | various | 3.0 | DECAF |
| Starbucks Coffee 18 | various | 7.1 | DECAF |
| Urth Caffé | Beverly Hills | 6.2 | DECAF |
| Starbucks Coffee 19 | various | 213.8 | CAF |
| Coffee Bean 8 | various | 8.1 | DECAF |
| Starbucks Coffee 20 | various | 7.4 | DECAF |
| Coffee Bean 9 | various | 5.6 | DECAF |

HPLC Data Statistics

| | |
|---|---|
| Mean | 16.03 |
| Standard Error | 7.22 |
| Median | 5.65 |
| Mode | 2.93 |
| Standard Deviation | 42.08 |
| Sample Variance | 1770.86 |
| Kurtosis | 17.24 |
| Skewness | 4.16 |
| Range | 212.25 |
| Minimum | 1.54 |
| Maximum | 213.79 |
| Sum | 545.09 |
| Count | 34.00 |
| True Caf | 3 |
| % True Caf | 8.8% |
| True Decaf | 31 |
| % True Decaf | 91.2% |

SLRC Strip Test Statistics

| | |
|---|---|
| Count | 34.00 |
| Correct vs HPLC | 32.00 |
| % Correct | 94.12 |
| % Correct (True Caf) | 100.00 |
| % Correct (True Decaf) | 93.55 |

High-End Restaurants

| Restaurant | Location | HPLC Result (mg/8 oz) | SLRC Test Strip Result (Caf/Decaf) |
|---|---|---|---|
| Grill on the Alley | Beverly Hills | 71.4 | CAF |
| The Palm | West Hollywood | 72.1 | CAF |
| Maple Drive Restaurant | Beverly Hills | 10.9 | DECAF |
| Pacific Dining Car | Los Angeles | 3.3 | DECAF |
| Patina | Los Angeles | 19.3 | DECAF |
| Providence | Los Angeles | 7.7 | DECAF |
| Boa Steakhouse | Santa Monica | 6.7 | DECAF |
| Michael's | Santa Monica | 16.0 | CAF |
| One Pico | Santa Monica | 35.2 | CAF |
| Valentino | Santa Monica | 6.1 | DECAF |
| Ivy at the Shore | Santa Monica | 38.5 | CAF |
| Whist at the Viceroy | Santa Monica | 14.4 | DECAF |
| Sunset Marquis | West Hollywood | 10.5 | DECAF |
| Hotel Bel Air | Los Angeles | 7.1 | DECAF |
| L'Ermitage Hotel | Beverly Hills | 6.7 | DECAF |
| Beverly Hilton | Beverly Hills | 148.3 | CAF |
| Peninsula Hotel | Beverly Hills | 4.6 | DECAF |
| Beverly Hills Hotel | Beverly Hills | 51.1 | CAF |
| Spago | Beverly Hills | 10.2 | DECAF |
| Chateau Hotel | West Hollywood | 9.5 | DECAF |
| Regent Beverly Hills | Beverly Hills | 3.8 | DECAF |
| Mondrian Hotel | West Hollywood | 3.0 | DECAF |
| Mandalay Bay Hotel | Las Vegas | 5.5 | DECAF |
| Mandalay Bay Hotel Red Square | Las Vegas | 92.8 | CAF |
| MGM Grand | Las Vegas | 244.2 | CAF |
| Wynn Hotel & Casino | Las Vegas | 325.1 | CAF |
| Caesar's Palace | Las Vegas | 37.9 | CAF |
| Bellini | Palm Dessert | 4.9 | DECAF |
| Cuistot | Palm Dessert | 29.5 | CAF |
| Ritz Carlton | Pasadena | 13.0 | DECAF |
| Devon 1 | Monrovia | 8.4 | DECAF |

-continued

| | | | |
|---|---|---|---|
| Devon 2 | Monrovia | 6.4 | DECAF |
| Water Grill | Los Angeles | 6.4 | DECAF |

HPLC Data Statistics

| | |
|---|---|
| Mean | 40.32 |
| Standard Error | 12.39 |
| Median | 10.55 |
| Mode | #N/A |
| Standard Deviation | 71.19 |
| Sample Variance | 5068.57 |
| Kurtosis | 9.14 |
| Skewness | 2.98 |
| Range | 322.15 |
| Minimum | 3.00 |
| Maximum | 325.15 |
| Sum | 1330.56 |
| Count | 33.00 |
| True Caf | 13 |
| % True Caf | 39.4% |
| True Decaf | 20 |
| % True Decaf | 60.6% |

SLRC Strip Test Statistics

| | |
|---|---|
| Count | 33.00 |
| Correct vs HPLC | 32.00 |
| % Correct | 96.97 |
| % Correct (True Caf) | 92.31 |
| % Correct (True Decaf) | 100.00 |

Medium-Price Restaurants

| Restaurant | Location | HPLC Result (mg/8 oz) | SLRC Test Strip Result (Caf/Decaf) |
|---|---|---|---|
| The Stinking Rose | Beverly Hills | 4.5 | DECAF |
| Houston's | Santa Monica | 5.1 | DECAF |
| Ocean Avenue Seafood | Santa Monica | 18.9 | CAF |
| Roy's | Los Angeles | 41.9 | CAF |
| Wood Ranch BBQ & Grill | Arcadia | 5.0 | DECAF |
| McGrath's Fish House | Arcadia | 15.8 | CAF |
| W Hotel | Los Angeles | 4.4 | DECAF |
| BJ's | Arcadia | 3.2 | DECAF |
| Cheesecake Factory | Pasadena | 2.3 | DECAF |
| California Pizza Kitchen | Pasadena | 12.6 | DECAF |
| IL Fornaio | Pasadena | 5.1 | DECAF |
| PF Chang's | Pasadena | 9.0 | DECAF |
| Claim Jumper | Arcadia | 4.5 | DECAF |
| Gordon Biersch Brewery | Pasadena | 50.1 | CAF |
| Westin | Los Angeles | 17.7 | CAF |
| McCormick & Schmick | Pasadena | 14.7 | CAF |
| The Derby | Arcadia | 66.1 | CAF |
| Whole Foods | Pasadena | 3.5 | DECAF |
| Cheesecake Factory | Beverly Hills | 3.8 | DECAF |
| California Pizza Kitchen | Beverly Hills | 8.5 | DECAF |
| Grand Lux Café | Beverly Hills | 3.5 | DECAF |
| PF Chang's | Beverly Hills | 5.1 | DECAF |
| The Farm of Beverly Hills | Beverly Hills | 6.2 | DECAF |
| Piccolo Paradiso | Beverly Hills | 1.5 | DECAF |
| Oliver Express Café | Beverly Hills | 2.9 | DECAF |
| Enoteca Drago | Beverly Hills | 93.4 | CAF |
| IL Pastaio | Beverly Hills | 3.6 | DECAF |
| Kate Mantilini | Beverly Hills | 13.5 | DECAF |
| La Meridien Café Noir | Beverly Hills | 5.4 | DECAF |
| Barney Greengrass | Beverly Hills | 7.2 | DECAF |
| Trilussa | Beverly Hills | 16.8 | CAF |
| Mako Sushi | Beverly Hills | 26.0 | CAF |
| Prego | Beverly Hills | 11.2 | DECAF |

HPLC Data Statistics

| | |
|---|---|
| Mean | 14.93 |
| Standard Error | 3.52 |
| Median | 6.15 |
| Mode | #N/A |
| Standard Deviation | 20.22 |
| Sample Variance | 408.85 |
| Kurtosis | 7.34 |
| Skewness | 2.65 |
| Range | 91.90 |
| Minimum | 1.55 |
| Maximum | 93.45 |
| Sum | 492.77 |
| Count | 33.00 |
| True Caf | 9 |
| % True Caf | 27.3% |
| True Decaf | 24 |
| % True Decaf | 72.7% |

SLRC Strip Test Statistics

| | |
|---|---|
| Count | 33.00 |
| Correct vs HPLC | 32.00 |
| % Correct | 96.97 |
| % Correct (True Caf) | 100.00 |
| % Correct (True Decaf) | 95.83 |

All Samples

HPLC Data Statistics

| | |
|---|---|
| Mean | 23.70 |
| Minimum | 1.55 |
| Maximum | 325.10 |
| Count | 100.00 |
| True Caf | 25 |
| % True Caf | 25.0% |
| True Decaf | 75 |
| % True Decaf | 75.0% |

SLRC Strip Test Statistics

| | |
|---|---|
| Count | 100.00 |
| Correct vs HPLC | 96.00 |
| % Correct | 96.00 |
| % Correct (True Caf) | 96.00 |
| % Correct (True Decaf) | 96.00 |

HPLC Method Precision

| | mg/8 oz | | | | | |
|---|---|---|---|---|---|---|
| Replicate | Sample 1 | Sample 2 | Sample 3 | Sample 4 | Sample 5 | Sample 6 |
| 1 | 2.184 | 5.232 | 7.848 | 9 | 31.584 | 49.032 |
| 2 | 3.096 | 5.208 | 7.472 | 8.952 | 31.32 | 48.816 |
| 3 | 2.256 | 5.28 | 7.3848 | 8.976 | 31.128 | 48.648 |
| 4 | 2.3 | 5.5 | 7.7 | 8.8 | 30.984 | 51.1 |
| Mean | 2.5 | 5.3 | 7.6 | 8.9 | 31.3 | 49.4 |
| SD | 0.43 | 0.14 | 0.21 | 0.09 | 0.26 | 1.12 |
| CV | 17.5 | 2.7 | 2.8 | 1.0 | 0.8 | 2.3 |

| | | mg/8 oz | | |
|---|---|---|---|---|
| Sample | N | Average | S.D. | C.V. % |
| 1 | 4 | 2.5 | 0.43 | 17.5 |
| 2 | 4 | 5.3 | 0.14 | 2.7 |
| 3 | 4 | 7.6 | 0.21 | 2.8 |
| 4 | 4 | 8.9 | 0.09 | 1.0 |
| 5 | 4 | 31.3 | 0.26 | 0.8 |
| 6 | 4 | 49.4 | 1.12 | 2.3 |

What is claimed is:

1. A method of detecting the presence of caffeine in a liquid sample, comprising:
   applying the liquid sample to a contact region of a testing substrate for detecting caffeine;
   flowing the liquid towards a signal region of the testing substrate spatially distinct from the contact region;

detecting the signal region a visible signal indicating for the liquid sample a caffeine level corresponding to a caffeinated beverage, wherein the detecting comprises an assay using anti-caffeine antibody having ATCC accession number PTA-9544; and wherein the visible signal is ready for detecting within three minutes of applying the liquid sample.

2. The method of claim 1, wherein the testing substrate materials are selected for enabling the detecting within three minutes.

3. The method of claim 1, wherein the caffeine level corresponding to a caffeinated beverage is at least 15 mg/8 oz.

4. The method of claim 1, wherein the visible signal comprises two separate signal areas.

5. The method of claim 1, wherein the testing substrate is contained within a housing.

6. The method of claim 1, wherein the antibody has a low cross reactivity with non-caffeine alkaloids.

* * * * *